(12) United States Patent
Prodhom et al.

(10) Patent No.: US 10,573,413 B2
(45) Date of Patent: Feb. 25, 2020

(54) METHOD FOR THE DETECTION AND HANDLING OF HYPOGLYCEMIA

(71) Applicants: Roche Diabetes Care, Inc., Indianapolis, IN (US); Roche Diagnostics International AG, Rotkreuz (CH)

(72) Inventors: Gilles Prodhom, Bern (CH); Bernhard Teupe, Bad Mergentheim (DE); Alan Greenburg, Indianapolis, IN (US); Maury Zivitz, Indianapolis, IN (US)

(73) Assignees: Roche Diabetes Care, Inc., Indianapolis, IN (US); Roche Diagnostics International AG, Rotkreuz (CH)

( * ) Notice: Subject to any disclaimer, the term of this patent is extended or adjusted under 35 U.S.C. 154(b) by 1710 days.

(21) Appl. No.: 13/803,465

(22) Filed: Mar. 14, 2013

(65) Prior Publication Data
US 2014/0278123 A1 Sep. 18, 2014

(51) Int. Cl.
*G16H 50/50* (2018.01)
*G16H 20/10* (2018.01)

(52) U.S. Cl.
CPC ............ *G16H 50/50* (2018.01); *G16H 20/10* (2018.01)

(58) Field of Classification Search
None
See application file for complete search history.

(56) References Cited

U.S. PATENT DOCUMENTS

| | | | |
|---|---|---|---|
| 4,731,726 A * | 3/1988 | Allen, III | A61B 5/14532 600/300 |
| 5,822,715 A * | 10/1998 | Worthington | G16H 50/50 702/19 |
| 6,923,763 B1 * | 8/2005 | Kovatchev | A61B 5/14532 600/300 |
| 2008/0177165 A1 | 7/2008 | Blomquist et al. | |
| 2008/0300534 A1 | 12/2008 | Blomquist et al. | |
| 2010/0268040 A1 * | 10/2010 | Ben-Oren | G16H 50/20 600/301 |
| 2010/0317952 A1 | 12/2010 | Budiman et al. | |
| 2011/0098548 A1 | 4/2011 | Budiman et al. | |
| 2012/0266251 A1 * | 10/2012 | Birtwhistle | G06F 19/323 726/26 |
| 2013/0041342 A1 | 2/2013 | Bernini et al. | |

FOREIGN PATENT DOCUMENTS

WO 2010/097796 A1 9/2010

OTHER PUBLICATIONS

Teupe, et al., Advice Device; Dec. 27, 2012; XP055143879; URL: http://www.diabetesdorfalthausen.de/Content/Advice-Device.pdf.

\* cited by examiner

*Primary Examiner* — Soren Harward
(74) *Attorney, Agent, or Firm* — Dinsmore & Shohl LLP

(57) ABSTRACT

A method is described herein to detect and treat hypoglycemia. An example of this method involves the detection of hypoglycemia in a patient with a computing device, computation of a recommended carbohydrate amount to ingest by the patient with the computing device in response to said detecting the hypoglycemia, output of the recommended carbohydrate amount with the computing device, and the performance of a hypoglycemia surveillance with the computing device to determine whether the recommended carbohydrate amount remedied the hypoglycemia.

35 Claims, 10 Drawing Sheets

METHOD FOR THE DETECTION AND HANDLING OF HYPOGLYCEMIA

BACKGROUND

Diabetics are always attempting to tightly control their blood glucose levels so as to avoid the detrimental effects of their condition. High blood glucose levels, commonly referred to as hyperglycemia, can for example lead to organ damage, ketoacidosis, and/or long term debilitating or life-threatening conditions. If left untreated, low blood glucose conditions, commonly referred to as hypoglycemia, can lead to unconsciousness or even death. To avoid these problems, diabetics typically monitor their blood glucose levels closely and sometimes make adjustments to their treatment regimen so as to avoid hypoglycemia and hyperglycemia. For example, when experiencing hypoglycemia, a health care provider (HCP) may recommend that a diabetic ingest a specific amount of carbohydrates (e.g., drink a specific amount of orange juice) in order to raise their blood glucose levels. However, follow up assessments to see if the hypoglycemia has been addressed sometimes does not occur. Moreover, the prescribed amount of carbohydrate may not be appropriate in some circumstances.

Hypoglycemia occurs when glucose is lacking in the blood plasma. Thus, hypoglycemia is usually detected by the use of spot monitoring by measuring blood glucose concentration. intracellular glucose deficiency (IGD) is caused by decreased performance of tissues whose cell plasma contains too little glucose. When an individual has excessive amounts of insulin, glucose migrates in the cells, thereby inducing a decrease in glucose concentration in both the blood plasma and the interstitial fluid (ISF). This in turn can lead to both hypoglycemia and intracellular glucose deficiency. Blood plasma glucose concentration (BG) and tissue glucose concentration (TG) vary as a function of endogenous glucose production and glucose consumption in the cells. However, such a change does not occur at the same time in blood and tissue. Consequently, there is a delay between changes in blood plasma glucose concentration and tissue glucose concentration. This delay varies depending on the tissue type but the average time difference can span up to 20 minutes and the difference in concentration can be estimated to about 30 mg/dL in up to 66% of the body locations. It should be recognized that this delay can create a whole host of issues in properly remedying a hypoglycemic event.

Thus, there is a need for improvement in this field.

SUMMARY

According to at least one exemplary embodiment of the present disclosure, a method of detecting and treating hypoglycemia is provided.

According to at least one embodiment of the method of the present disclosure, the method, comprises detecting hypoglycemia in a patient with a computing device based at least on the patient having a symptom of hypoglycemia, receiving with the computing device a blood glucose measurement of the patient, computing a recommended carbohydrate amount to ingest by the patient with the computing device in response to said detecting the hypoglycemia, wherein the recommended carbohydrate amount is based at least in part on the blood glucose measurement of the patient, and outputting the recommended carbohydrate amount with the computing device.

According to at least one embodiment of the method of the present disclosure, the method comprises receiving with a computing device a blood glucose measurement of a patient, computing a recommended carbohydrate amount to ingest by the patient with the computing device, wherein the recommended carbohydrate amount is based at least on the blood glucose measurement of the patient, wherein said computing the recommended carbohydrate amount includes adjusting the recommended carbohydrate amount based on an amount of carbohydrates consumed by the patient during a timeframe, and outputting the recommended carbohydrate amount with the computing device.

According to at least one embodiment of the method of the present disclosure, the method, comprises detecting hypoglycemia in a patient with a computing device, computing a recommended carbohydrate amount to ingest by the patient with the computing device in response to said detecting the hypoglycemia, outputting the recommended carbohydrate amount with the computing device, and performing hypoglycemia surveillance with the computing device to determine whether the recommended carbohydrate amount remedied the hypoglycemia.

In at least one embodiment of the present disclosure, computating the recommended carbohydrate amount includes adjusting the recommended carbohydrate amount based on amount of carbohydrates consumed by the patient during a timeframe.

In at least one embodiment of the present disclosure, the method further comprises performing hypoglycemia surveillance with the computing device to determine whether the recommended carbohydrate amount remedied the hypoglycemia.

In at least one embodiment of the present disclosure, the hypoglycemia surveillance includes receiving with the computing device a second blood glucose measurement of the patient after said computing the recommended carbohydrate amount and determining with the computing device that the hypoglycemia has been remedied based at least on the second blood glucose measurement.

In at least one embodiment of the present disclosure, the method further comprises receiving with the computing device data indicating that the patient lacks hypoglycemia symptoms after said computing the recommended carbohydrate amount and determining with the computing device that the hypoglycemia has been remedied based at least on the lack of the hypoglycemia symptoms.

In at least one embodiment of the present disclosure, the method further comprises delaying said performing the hypoglycemia surveillance for a delay period.

In at least one embodiment of the present disclosure, the delay period is at least 15 minutes.

In at least one embodiment of the present disclosure, the method further comprises ending said performing the hypoglycemia surveillance when the second blood glucose measurement exceeds a surveillance end threshold.

In at least one embodiment of the present disclosure, the surveillance end threshold is 100 mg/dl.

In at least one embodiment of the present disclosure, the method further comprises ending said performing the hypoglycemia surveillance when the second blood glucose measurement exceeds a relative threshold that varies based on amount of carbohydrates previously consumed.

In at least one embodiment of the present disclosure, the relative threshold is based on a time dependent carbohydrate absorption function that increases with time.

In at least one embodiment of the present disclosure, the method further comprises calculating with the computing device the relative threshold using the following formula $$BG_{end,relative} = \gamma(t-t_1) \cdot BG_{hypo,end} + (1-\gamma(t-t_1)) \cdot BG_0$$

where:
$BG_{end,relative}$=Relative threshold for ending the surveillance phase;
$BG_{hypo,end}$=Threshold where hypoglycemia is considered ended;
$\gamma(x)$=Carbohydrate absorption function for time interval x;
t=Current time when relative threshold is being calculated;
$t_1$=Time when first carbohydrate recommended or consumed; and
$BG_0$=Original blood glucose measurement.

In at least one embodiment of the present disclosure, the method further comprises receiving a third blood glucose measurement, and calculating with the computing device the relative threshold using the following formula $$BG_{end,relative} = \gamma(t-t_2) \cdot BG_{hypo,end} +$$
$$(1-\gamma(t-t_2)) \cdot BG_2 + \frac{\gamma(t-t_2)}{\gamma(t_2-t_1)}(\gamma(t-t_1)-1)(BG_2 - BG_1)$$

where:
$BG_{end,relative}$=Relative threshold for ending the surveillance phase;
$BG_{hypo,end}$=Threshold where hypoglycemia is considered ended;
$\gamma(x)$=Carbohydrate absorption function for time interval x;
t=Current time when relative threshold is being calculated;
$t_n$=Time of $n^{th}$ measurement since hypoglycemia; and
$BG_n$=$n^{th}$ blood glucose measurement since hypoglycemia.

In at least one embodiment of the present disclosure, the recommended carbohydrate amount is selected from a group consisting of a small carbohydrate amount, a medium carbohydrate amount, and a large carbohydrate amount.

In at least one embodiment of the present disclosure, the method further comprises normalizing the recommended carbohydrate amount based on patient weight.

In at least one embodiment of the present disclosure, the method further comprises adjusting the recommended carbohydrate amount based on patient weight risk of fainting during hypoglycemia.

In at least one embodiment of the present disclosure, the method further comprises adjusting the recommended carbohydrate amount based on a total daily dose of insulin by the patient.

In at least one embodiment of the present disclosure, the method further comprises calculating with the computing device the recommended carbohydrate amount using the following formula $$\begin{cases} n_{BU,small} = f_n(n_{BU,TDD} + n_{BU,fainting}) \\ n_{BU,medium} = f_n(n_{BU,TDD} + n_{BU,fainting} + 1) \\ n_{BU,large} = f_n(n_{BU,TDD} + n_{BU,fainting} + 2) \end{cases}$$

where:
$n_{BU,small}$=Small amount of carbohydrate;
$n_{BU,medium}$=Medium amount of carbohydrate;
$n_{BU,large}$=Large amount of carbohydrate;
$f_n$=Normalization factor based on patient weight;
$n_{BU,fainting}$=Risk of fainting additional bread unit; and
$n_{BU,TDD}$=Additional bread unit recommended for patients with a total daily dose (TDD) of insulin ≤30 UI.

In at least one embodiment of the present disclosure, computing the recommended carbohydrate amount includes selecting the small carbohydrate amount, the medium carbohydrate amount, and the large carbohydrate amount based on a very low blood glucose limit, a low blood glucose limit, and a medium-low blood glucose limit.

In at least one embodiment of the present disclosure, the very low blood glucose limit, the low blood glucose limit, and the medium-low blood glucose limit are respectively 60 mg/dl, 100 mg/dl, and 140 mg/dl.

In at least one embodiment of the present disclosure, the method further comprises calculating with the computing device the recommended carbohydrate amount using the following formula $$n_{BU} = \begin{cases} 0 & \text{if } BG_{ml} < BG \\ n_{BU,small} & \text{if } BG_1 < BG \leq BG_{ml} \\ n_{BU,medium} & \text{if } BG_{vl} < BG \leq BG_1 \\ n_{BU,large} & \text{if } BG \leq BG_{vl} \end{cases} \quad \text{Equation 21}$$

where:
$n_{BU}$=Amount of carbohydrate;
$n_{BU,small}$=Small amount of carbohydrate;
$n_{BU,medium}$=Medium amount of carbohydrate;
$n_{BU,large}$=Large amount of carbohydrate;
$BG_1$=Blood glucose measurement at hypoglycemia detection;
$B_{ml}$=Medium-low blood glucose range limit;
$BG_1$=Low blood glucose range limit; and
$BG_{vl}$=Very low blood glucose range limit.

In at least one embodiment of the present disclosure, computing the recommended carbohydrate amount includes adjusting the recommended carbohydrate amount based on prior blood glucose measurements made after detecting the hypoglycemia, prior amounts of carbohydrates ingested, and a carbohydrate absorption function.

In at least one embodiment of the present disclosure, the method further comprises receiving a second blood glucose measurement after the patient ingested the second recommended amount of carbohydrate and calculating with the computing device a second recommended carbohydrate amount using the following formula $$\begin{cases} BG_{vl,2} = \gamma(t-t_1) \cdot BG_{vl,1} + (1-\gamma(t-t_1)) \cdot BG_1 \\ BG_{l,2} = \gamma(t-t_1) \cdot BG_{l,1} + (1-\gamma(t-t_1)) \cdot BG_1 \\ BG_{ml,2} = \gamma(t-t_1) \cdot BG_{ml,1} + (1-\gamma(t-t_1)) \cdot BG_1 \end{cases}$$

where:
$BG_{vl,2}$=Very low blood glucose range limit or threshold for a second amount of carbohydrate;
$BG_{l,2}$=Low blood glucose range limit or threshold for a second amount of carbohydrate;
$BG_{ml,2}$=Medium-low blood glucose range limit or threshold for a second amount of carbohydrate;
$\gamma(x)$=Carbohydrate absorption function for time interval x;
t=Current time when relative threshold is being calculated;
$t_1$=Time when first carbohydrate was consumed; and
$BG_1$=First blood glucose measurement.

In at least one embodiment of the present disclosure, the method further comprises receiving a third blood glucose measurement after the patient ingested the second recommended amount of carbohydrate and calculating with the computing device a third recommended carbohydrate amount using the following formula $$\begin{cases} BG_{vl,3} = \gamma(t-t_2) \cdot BG_{vl,3} + (1-\gamma(t-t_2)) \cdot BG_2 + \dfrac{\gamma(t-t_2)}{\gamma(t_2-t_1)}(\gamma(t-t_1)-1)(BG_2-BG_1) \\ BG_{l,3} = \gamma(t-t_2) \cdot BG_{l,3} + (1-\gamma(t-t_2)) \cdot BG_2 + \dfrac{\gamma(t-t_2)}{\gamma(t_2-t_1)}(\gamma(t-t_1)-1)(BG_2-BG_1) \\ BG_{ml,3} = \gamma(t-t_2) \cdot BG_{ml,3} + (1-\gamma(t-t_2)) \cdot BG_2 + \dfrac{\gamma(t-t_2)}{\gamma(t_2-t_1)}(\gamma(t-t_1)-1)(BG_2-BG_1) \end{cases}$$

where:
$BG_{vl,3}$=Very low blood glucose range limit or threshold for a third amount of carbohydrate (i.e., at time t3);
$BG_{l,3}$=Low blood glucose range limit or threshold for a third amount of carbohydrate (i.e., at time t3);
$BG_{ml,3}$=Medium-low blood glucose range limit or threshold for a third amount of carbohydrate (i.e., at time t3);
$\gamma(x)$=Carbohydrate absorption function for time interval x;
t=Current time when relative threshold is being calculated;
$t_n$=Time of $n^{th}$ measurement since hypoglycemia; and
$BG_n$=$n^{th}$ blood glucose measurement since hypoglycemia.

In at least one embodiment of the present disclosure, the method further comprises calculating subsequent amounts of carbohydrates by superimposing the effects of previous carbohydrate amounts.

In at least one embodiment of the present disclosure, the method further comprises calculating the very low blood glucose limit, the low blood glucose limit, and the medium-low blood glucose limit based on no more than the last three blood glucose measurements.

In at least one embodiment of the present disclosure, the method further comprises calculating with the computing device the carbohydrate absorption function using the following formula $$\begin{cases} \gamma(x) = 0 & \text{if } x = 0 \\ \gamma(x) = -0.000125 \cdot x^2 + 0.022525 \cdot x + 0.0019 & \text{if } 0 < x < 78 \\ \gamma(x) = 1 & \text{if } x \geq 78 \end{cases}$$

where:
$\gamma(x)$=Carbohydrate absorption function; and
x=Time frame of interest (in minutes).

In at least one embodiment of the present disclosure, the method further comprises calculating with the computing device the carbohydrate absorption function using the following formula $$\begin{cases} \gamma(x) = -\dfrac{1}{t_a^2}x^2 + \dfrac{2}{t_a}x & \text{if } 0 \leq x \leq t_a \\ \gamma(x) = 1 & \text{if } x > t_a \end{cases}$$

where:
$\gamma(x)$=Carbohydrate absorption function;
x=Time frame of interest (in minutes); and
$t_a$=Total carbohydrate absorption time.

In at least one embodiment of the present disclosure, the method further comprises calculating with the computing device the carbohydrate absorption function using the following formula $$\begin{cases} \gamma(x) = \dfrac{1}{t_a}x & \text{if } 0 \leq x \leq t_a \\ \gamma(x) = 1 & \text{if } x > t_a \end{cases}$$

where:
$\gamma(x)$=Carbohydrate absorption function;
x=Time frame of interest (in minutes); and
$t_a$=Total carbohydrate absorption time.

In at least one embodiment of the present disclosure, the method further comprises calculating with the computing device the carbohydrate absorption function using the following formula $$\gamma(x) = 1 - e^{-a \cdot x}$$

where:
$\gamma(x)$=Carbohydrate absorption function;
x=Time frame of interest (in minutes); and
a=0.03.

In at least one embodiment of the present disclosure, the method further comprises calculating with the computing device the carbohydrate absorption function using the following formula $$\gamma(x) = 1 - e^{-ax^2 - bx}$$

where:
$\gamma(x)$=Carbohydrate absorption function;
x=Time frame of interest (in minutes);
a=0.0004; and
b=0.015.

In at least one embodiment of the present disclosure, the carbohydrate absorption function is a linear function.

In at least one embodiment of the present disclosure, the carbohydrate absorption function is a parabolic function.

In at least one embodiment of the present disclosure, the carbohydrate absorption function is an exponential function.

In at least one embodiment of the present disclosure, the method further comprises receiving with the computing device a manual input that the patient has the symptom of hypoglycemia.

In at least one embodiment of the present disclosure, the method further comprises determining automatically with the computing device that the patient has the symptom of hypoglycemia.

In at least one embodiment of the present disclosure, said determining automatically includes analyzing results from a questionnaire to detect hypoglycemic symptoms with the computing device.

In at least one embodiment of the present disclosure, said determining automatically includes analyzing a video of the patient for the hypoglycemic symptoms with the computing device.

In at least one embodiment of the present disclosure, said determining automatically includes analyzing speech of the patient for the hypoglycemic symptoms with the computing device.

In at least one embodiment of the present disclosure, the computing device includes a glucose meter, a computer, an insulin pump, or a combination of the above.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein.

DESCRIPTION OF THE SELECTED EMBODIMENTS

Figure 1:
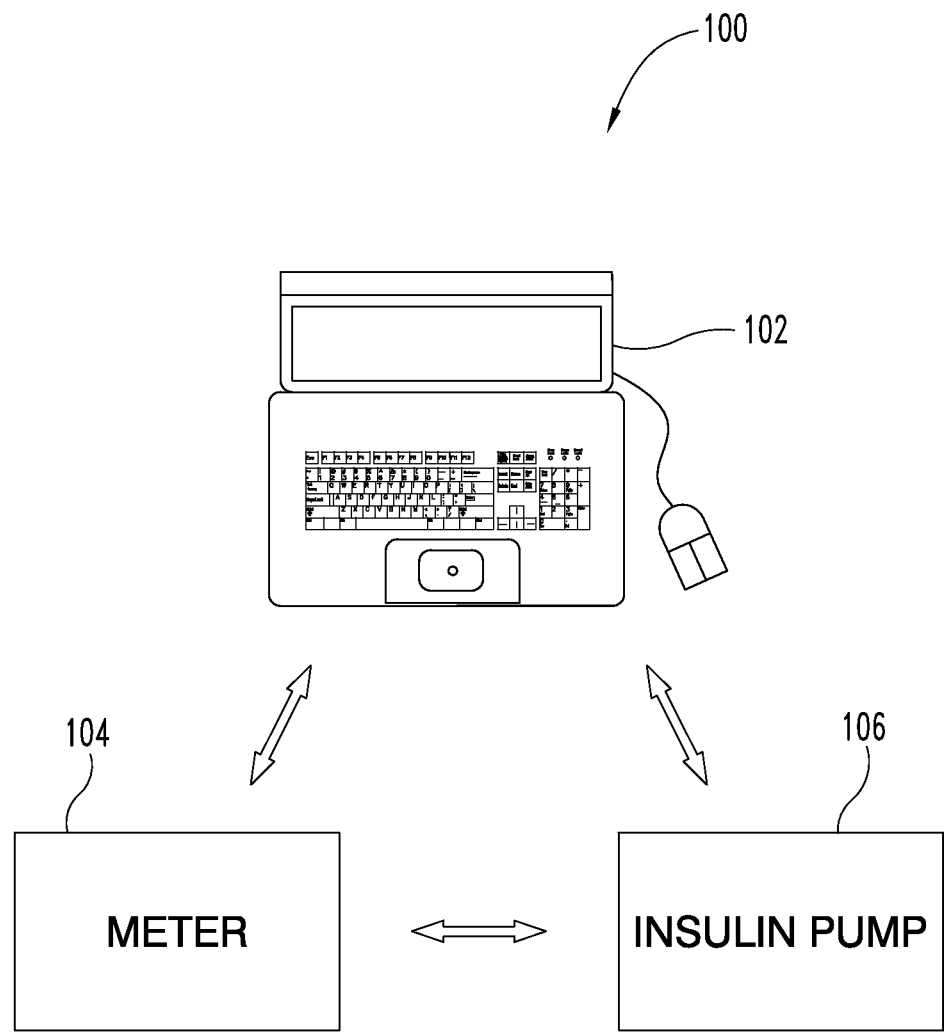
FIG. 1 is a diagrammatic view of a blood glucose monitoring system, according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. For instance, logical, mechanical, and electrical changes may be made without departing from the spirit and scope of the present disclosure.

Usual methods for hypoglycemia detection only monitor blood glucose measurements. Typical treatments for hypoglycemia include recommendations of carbohydrate ingestion if the measured blood glucose level is below a specific threshold. Such a threshold is usually set by a health care provider and does not vary as a function of time. Common methods for treating hypoglycemia do not necessarily include follow up blood glucose measurements for the patient in order to verify that patient is no longer hypoglycemic. Moreover, the calculation of carbohydrate amounts in case of hypoglycemia are based on fixed thresholds for blood glucose concentrations assessments and do not consider prior information, such as previous amounts of carbohydrates consumed. Moreover, common hypoglycemia detection and treatment methodologies fail to consider delays between carbohydrate consumption and changes in glucose levels. Questionable treatment recommendations can occur if the blood glucose readings are measured in a small time interval.

In various methods of detecting and treating hypoglycemia as described herein, method allows the detection of hypoglycemia by considering the patient's feeling of hypoglycemia. This allows patient support to occur in the very early phase of hypoglycemia. In addition, the method supports the patient in the hypoglycemia recovery stage by recommending the ingestion of multiple carbohydrate amounts computed by using an original model taking blood glucose dynamics and previous carbohydrate ingestion into account.

As mentioned before, the method of detecting and treating hypoglycemia described herein helps to reduce the length of or even eliminate hypoglycemic events as well as ensures that the hypoglycemia has been resolved. The method includes three general phases, a detection phase, a carbohydrate computation phase, and a surveillance phase. In the detection phase, the method not only considers blood glucose measurements but also whether the patient feels the onset of hypoglycemia. This may allow treatment to occur earlier and at higher blood glucose levels, thereby minimizing the length of or even avoiding a hypoglycemia event altogether. For the carbohydrate computation phase, the recommended carbohydrate amount can be adjusted based on the amount of carbohydrates recently consumed by the individual and/or recent blood glucose readings. The method also has a surveillance phase to determine whether the specified treatment option has remedied the hypoglycemia or additional treatment is required. The surveillance phase can include a delay so as to reduce the chance of making questionable recommendations based on glucose measurements being made too close together. Further, the surveillance and computation phases may in some instances repeat until the patient is no longer experiencing hypoglycemia.

An exemplary embodiment of a system 100 for performing the hypoglycemia detection and treatment method is illustrated in FIG. 1. As shown, the system 100 includes a computer 102, a glucose meter 104, and an insulin pump 106. The computer 102 is used to collect and analyze data from the glucose meter 104 and/or the insulin pump 106. The glucose meter 104 is used to collect blood glucose readings from the patient, and the insulin pump 106 is used to deliver insulin to the patient. As depicted by the arrows in FIG. 1, the computer 102 is configured to communicate with the glucose meter 104 and the insulin pump 106 in any number of manners, such as through a wired and/or wireless connection.

In the illustrated embodiment, the computer 102 includes at least one processor that executes software and/or firmware code stored in memory of computer 102. The software/firmware code contains instructions that, when executed by the processor of computer 102, causes computer 102 to perform the functions described herein. For example, computer 102 may have various types of software, including but not limited to CareLink® Pro, DexCom DM® 3, and Abbott Copilot® brand software to name just a few examples. Computer 102 may alternatively include one or more application-specific integrated circuits (ASICs), field-programmable gate arrays (FPGAs), digital signal processors (DSPs), hardwired logic, or combinations thereof. While computer 102 is illustratively a personal computer, other suitable devices may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although computer 102 is illustrated as a single computing device, multiple computing devices may be used together to perform the functions of computer 102 described herein.

As depicted by the arrows in FIG. 1, the computer 102 is configured to communicate with the meter 104 and/or the pump 106 in any number of manners, such as through a wired and/or wireless connection. Such wireless communications may be radio frequency ("RF") or other suitable wireless frequency, in which the measured glucose results are transmitted via electromagnetic waves. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. The communication may be unidirectional (i.e., data is transmitted only from meter 104 to computer 102) or bidirectional (i.e., data is transmitted between meter 104 and computer 102 in either direction). Furthermore, the communication may also facilitate communication between two or more devices, such as between meter 104, computing device 102, pump 106, and other suitable devices or systems. In addition, a wired link may alternatively be provided, such as, for example, a wired Ethernet link. Other suitable public or proprietary wired or wireless links may also be used. The connection may be used to transmit data such as blood glucose measurements or results from a process performed on blood glucose measurement data. The connection may also be used to configure the parameters or settings on meter 104 and/or the insulin pump 108.

In at least one embodiment, computer 102 is in communication with a remote computing device, such as at a caregiver's facility or a location accessible by a caregiver, and data (e.g., glucose data or other physiological information) is transferred between them. In this embodiment, computer 102 and the remote device are configured to transfer physiological information through a data connection such as, for example, via the Internet, cellular communications, or the physical transfer of a memory device such as a diskette, USB key, compact disc, or other portable memory device.

In one particular example, the glucose meter 104 includes an ACCU-CHEK® Expert brand meter. The ACCU-CHEK® Expert brand meter is capable of storing glucose, meal, insulin, and other event information. All of this information can be easily uploaded to the computer 102 where the data can undergo further analysis and interpretation. It nevertheless should be appreciate that other kinds of meters can be used.

The insulin pump 106 can be connected to the glucose meter 104 and/or the computer 102. The connection may be used to transmit data from the blood glucose meter 104 and/or the computer 102 to the insulin pump 106 or vice versa. For example, the electronic connection may also be used to transmit instructions from the blood glucose meter 104 to the insulin pump 106 regarding one or more injections of insulin from the pump into the patient. Additionally, the connection may transmit information regarding past, present, or future injections or insulin levels from the insulin pump 106 to the glucose meter 104 and/or the continuous glucose monitoring meter 106. Similar to the electronic connection discussed above, the connection between the blood glucose meter 104 and the insulin pump 106 may be wired or wireless and may be the same or a different type of connection than the one between the meter 104 and the computer 102. It should be recognized that the system 100 in other embodiments can include different components, combinations of other components, and/or configured differently than is shown in FIG. 1.

Figure 2:
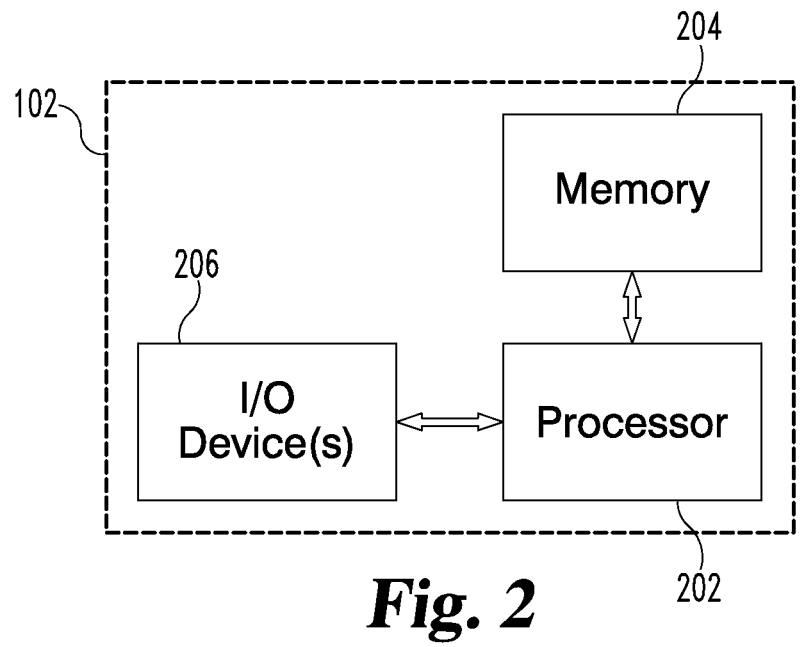
FIG. 2 is a block diagram of a computer used in the FIG. 1 system, according to at least one embodiment of the present disclosure.

FIG. 2 illustrates a block diagram of one example of the computer 102 illustrated in FIG. 1. As shown, the computer 102 includes a processor 202, memory 204, and/or an input/output (I/O) device(s) 206. The processor 202 is used to process information and commands, and the memory 204 stores data, such as glucose readings, structured tests, various functions, and procedures. For instance, the processor 202 can include a microprocessor and/or other electronics that are configured to process data, and the memory 204 is used to store data on a permanent or temporary basis.

The memory 204 is any suitable computer readable medium that is accessible by the processor 202. The memory 204 may be a single storage device or multiple storage devices, may be located internally or externally to computer 102, and may include both volatile and non-volatile media.

Further, the memory 204 may include one or both of removable and non-removable media. Exemplary memory 204 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by computer 102.

The I/O device(s) 206 is used to enter data and provide information. The I/O device 206 can include a tactile input, buttons, touch screens, displays, speakers, and/or printers, but it can also include other types of I/O devices. It should be appreciated that the computer 102 can include other components and/or be configured differently in other embodiments.

I/O device 206 in an exemplary embodiment may display the estimated glucose state of the person and/or a predicted glucose state of the person at some time in the future. The glucose state may include the estimated glucose level and/or the estimated rate-of-change of the glucose level. The displayed information may also include an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 milligrams of glucose per deciliter of blood (mg/dl). Computer 102 may also be configured to tactilely communicate information or warnings to the person, such as for example by vibrating.

Figure 3:
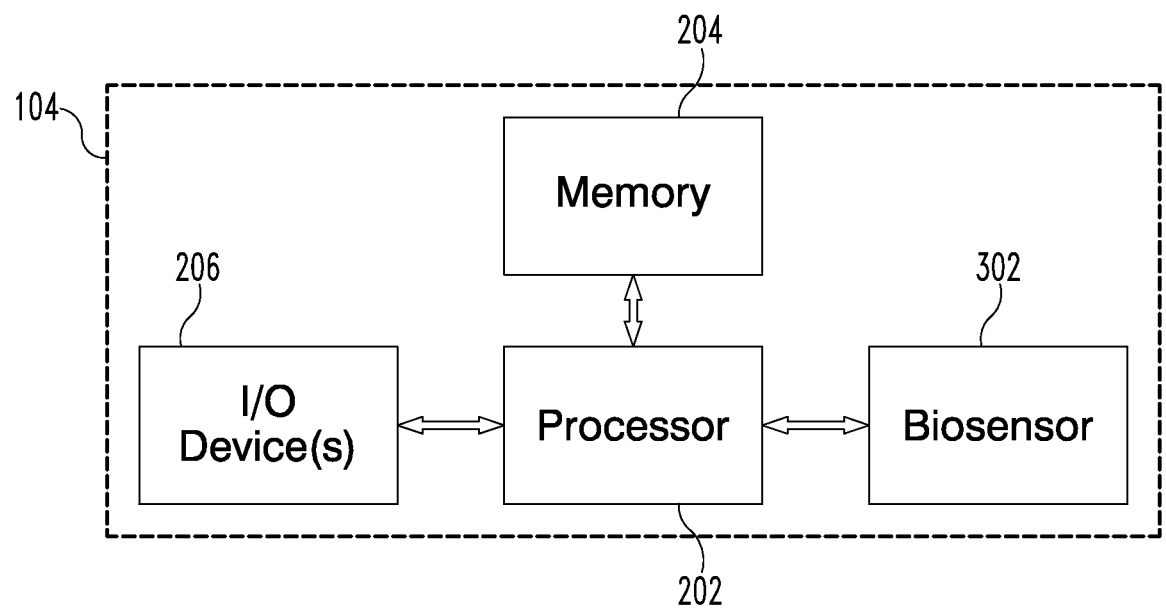
FIG. 3 is a block diagram of a meter used in the FIG. 1 system, according to at least one embodiment of the present disclosure.

FIG. 3 is a block diagram showing one example of the glucose meter 104 with a biosensor 302 for analyzing a body fluid sample so as to determine the blood glucose level. Depending on the type of meter, the biosensor 302 can include a discrete test strip and/or continuous monitoring probe. As illustrated, the meter 104 includes the processor 202, memory 204, and an input/output (I/O) device(s) 206 of the type described above. The processor 202 is used to process information and commands for analyzing body fluid samples, and the memory 204 stores information, such as blood glucose measurements, and other information.

Figure 4:
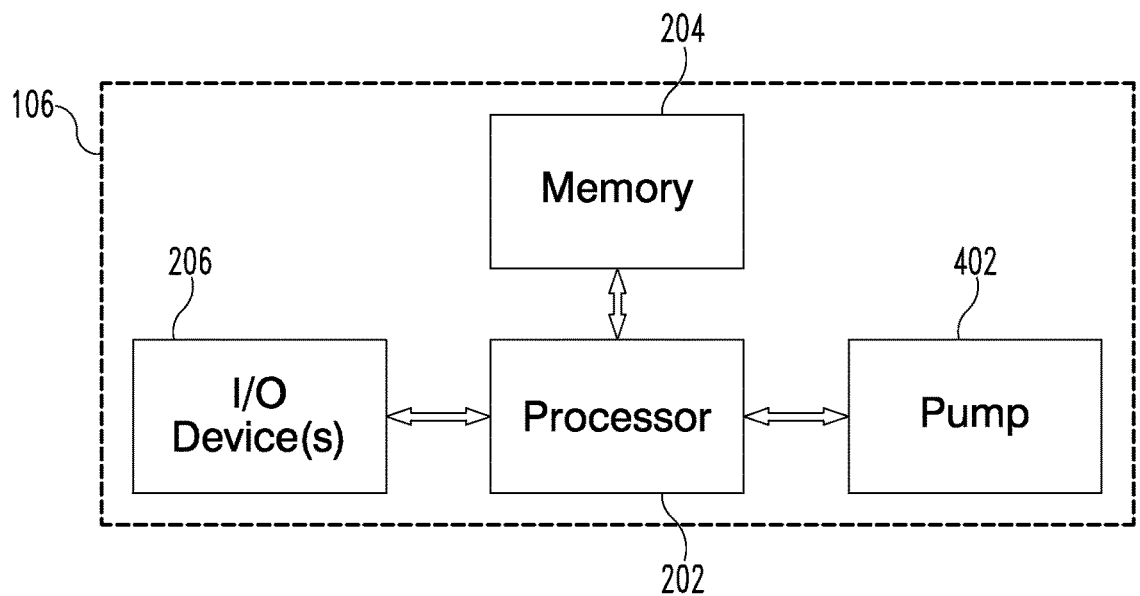
FIG. 4 is a block diagram of an insulin pump used the in the FIG. 1 system, according to at least one embodiment of the present disclosure.

FIG. 4 illustrates a block diagram of one example of the insulin pump 106 illustrated in FIG. 1. As shown, the insulin pump 106 includes a processor 202, memory 204, an input/output (I/O) device(s) 206, and a pump mechanism 402. The processor 202 is used to process information and commands, and the memory 204 stores data, various functions, and procedures. The I/O device(s) 206, such as one or more buttons, keyboards, and displays, is used to enter data and provide information as well as control the insulin pump 106. The pump mechanism 402 is controlled by the processor 202 so as to deliver the appropriate amount of insulin to the patient at the appropriate time.

The method of detecting and treating hypoglycemia will be initially described with reference to flowchart 500 in FIG. 5. As can be seen, the flowchart 500 shows the general phases of the method that include hypoglycemia detection 502, carbohydrate computation 504, and hypoglycemia surveillance 506 phases. During the detection phase 502, the glucose meter 104 is used to monitor the blood glucose levels of the patient. In addition, via the I/O device 206 of the meter 104, the patient can indicate whether they are feeling the effects of hypoglycemia. For example, the patient can press a button on the meter 104 when they feel the symptoms of hypoglycemia, such as feeling confused, feeling shaky, having blurred vision, etc. Upon receiving a notification that the patient is feeling hypoglycemic, the meter 104 in certain embodiments will instruct the patient to take a blood glucose measurement or the meter 104 can automatically perform the blood glucose measurement. This allows the meter 104 to determine if a significant hypoglycemic event is occurring. Moreover, the blood glucose readings help with computing the amount of carbohydrates to consume in the carbohydrate computation phase 504. If the measured blood glucose readings fall below a specified threshold ($BG_{hypo,detection}$) and/or the patient indicates having hypoglycemia symptoms, the meter 104 proceeds to the carbohydrate computation phase 504. Otherwise, the meter 104 continues in the detection phase 502 by monitoring for low blood glucose levels and/or hypoglycemia symptoms in the patient. As mentioned before, by monitoring both the blood glucose levels of the patient and for hypoglycemia symptoms of the patient, this method is able to detect and treat hypoglycemia at earlier stages of the condition. For example, the patient may notice that they are having hypoglycemia symptoms before their blood glucose level drops below the threshold. Conversely, the blood glucose level of the patient may drop below the threshold before the patient experiences any symptoms of hypoglycemia. As a result, the patient can be treated even before they are technically experiencing hypoglycemia.

Upon detection of hypoglycemia in stage 502, either by the blood glucose measurement or patient symptom route, the meter 104 proceeds to the carbohydrate computation phase 504. For explanation purposes, the amount of carbohydrates will be expressed in bread units. A bread unit is generally equivalent to 12 grams of carbohydrates. It should be appreciated that other scales can be used to represent the amount of carbohydrates to ingest. The meter 104 in stage 504 can recommend to the patient an initial amount of carbohydrate to consume (or not) based on the measured blood glucose level or even other factors. For instance, the meter 104 can recommend that the patient consume a large amount carbohydrates when well below the hypoglycemia threshold level and lesser amounts when above the threshold. These recommended carbohydrate amounts can be on a discrete or continuous scale. In another variation, the meter 104 in the carbohydrate computation phase 504 may consider the amount of recently consumed food, such as by questioning the patient about meals recently consumed. Such recently consumed food may in at least one embodiment be in a timeframe that is selected from the last 15 minutes, the last 30 minutes, the last 1 hour, the last 2 hours, the last 4 hours, the last 8 hours and the last 12 hours. In some instances, the patient may feel hypoglycemic but the blood glucose readings indicate otherwise. In such a case, the meter 104 may indicate that the patient does not need to consume any carbohydrates but may provide other recommendations, such as seeking additional medical treatment, or not.

After recommending the initial carbohydrate amount, the meter 104 checks to see if the hypoglycemia has been remedied in the hypoglycemia surveillance phase 506. As mentioned before, the hypoglycemia surveillance phase 506 includes a delay (e.g., 15 minutes) between consecutive measurements so as to compensate for delays that naturally occur, like the delays in absorbing the carbohydrates as well as delays between changes in blood plasma glucose concentration and tissue glucose concentration. During the hypoglycemia surveillance phase 506, the meter 104 not only monitors the blood glucose level of the patient but also how the patient feels. For example, after 15 to 20 minutes from recommending the patient to ingest the first or initial carbohydrate amount, the meter 104 can instruct the patient to perform (or automatically perform) a second blood glucose measurement ($BG_2$) as well as question the patient as to how they feel via the I/O device 206. If the patient is no longer feeling hypoglycemic and the second blood glucose reading ($BG_2$) is at or above a target blood glucose level, the meter 104 then can consider the hypoglycemia as being remedied, and if necessary, return to the hypoglycemia detection phase 502.

In one variation, the hypoglycemia surveillance phase 506 ends when the blood glucose measurement (BG) is above a specified threshold ($BG_{hypo,end}$). Equation 1 below represents this test.

$$BG \geq BG_{hypo,end} \quad \text{Equation 1}$$

where:
BG=Blood glucose measurement; and
$BG_{hypo,end}$=Threshold where hypoglycemia is considered ended.

This threshold ($BG_{hypo,end}$) for ending the surveillance phase 506 is typically larger than the threshold used to detect the hypoglycemia ($BG_{hypo,detection}$). In one example, the threshold used to detect the hypoglycemia ($BG_{hypo,detection}$) is 70 mg/dl, and the threshold ($BG_{hypo,end}$) for ending the surveillance phase 506 is 100 mg/dl.

Alternatively or additionally, the surveillance phase 506 can end when the blood glucose reading (BG) exceeds a second, relative threshold ($BG_{end,relative}$) that varies depending on the amount of carbohydrates previously consumed. When food is digested, it takes time for the food to be adsorbed into the blood stream so as to effect blood glucose measurements. If the measured blood glucose level is above this second, relative threshold ($BG_{end,relative}$) at a specified time after consuming a previously recommended carbohydrate amount, it would be expected that the blood glucose levels would continue to rise until eventually reaching in the near future the threshold where hypoglycemia is considered ended ($BG_{hypo,end}$). This test can be represented by Equation 2 below.

$$BG \geq BG_{end,relative} \quad \text{Equation 2}$$

where:
BG=Blood glucose measurement; and
$BG_{end,relative}$=Relative threshold for ending the surveillance phase.

In order to determine the relative threshold ($BG_{end,relative}$), a time dependent carbohydrate absorption function ($\gamma(t)$) is used to model the absorption of the carbohydrates. The carbohydrate absorption function ($\gamma(t)$) is initially zero (i.e., $\gamma(t)=0$), and monotonically increases toward one (i.e., $\gamma(t \to \infty)=1$).

Figure 6:
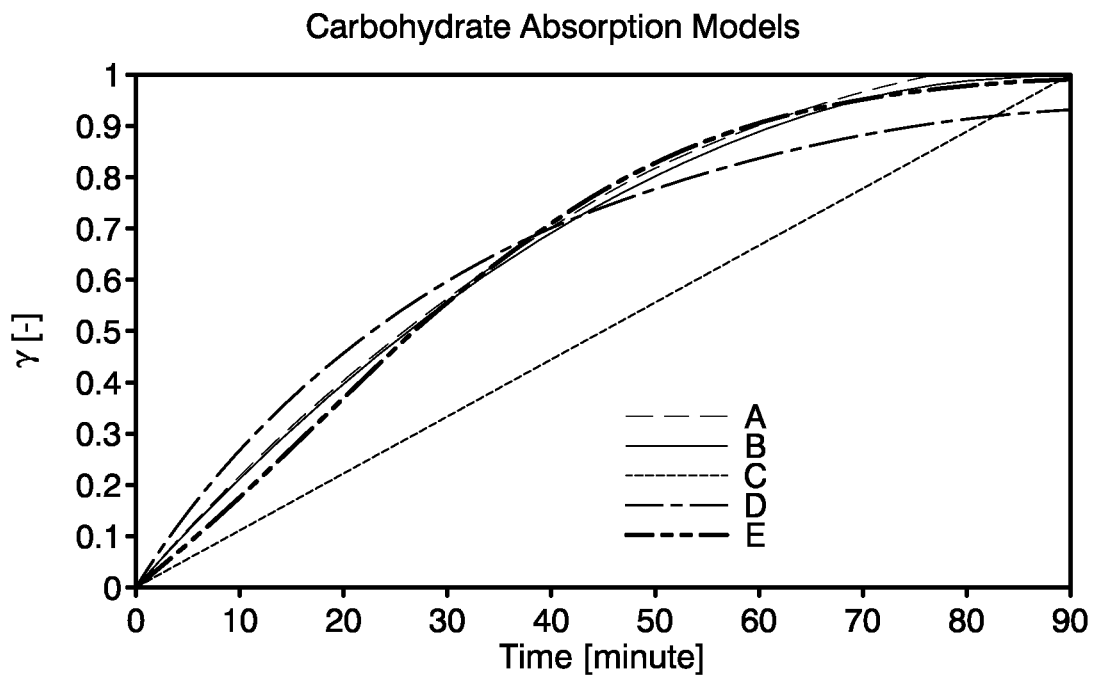
FIG. 6 is a graph comparing five functions for modeling carbohydrate absorption, according to at least one embodiment of the present disclosure.

FIG. 6 illustrates five different examples of this carbohydrate absorption function ($\gamma(t)$) for modeling carbohydrate absorption over time. It should be appreciated that these are just a few examples and other different functions can be used as well. As can be seen, all of the illustrated functions start initially having a zero (0) value when the carbohydrate is first consumed and approaches one (1) as time passes. In other words, when the carbohydrate or food is first eaten, the body is unable to instantaneously absorb the food, but as time passes, greater amounts of the food are absorbed, thereby increasing the blood glucose levels in the patient over time.

Model A in FIG. 6 is modeled by a function in which it is assumed all of the carbohydrates are completely absorbed in 78 minutes. The carbohydrate absorption function ($\gamma(x)$) for model A is shown in Equation 3 below. For the equations below, the generic term "x" has been to signify the particular time of interest because these functions can be used for different time intervals.

$$\begin{cases} \gamma(x) = 0 & \text{if } x = 0 \\ \gamma(x) = -0.000125 \cdot x^2 + 0.022525 \cdot x + 0.0019 & \text{if } 0 < x < 78 \\ \gamma(x) = 1 & \text{if } x \geq 78 \end{cases} \quad \text{Equation 3}$$

where:
$\gamma(x)$=Carbohydrate absorption function; and
x=Time frame of interest (in minutes).

The carbohydrate absorption function ($\gamma(x)$) for model A can be generalized to any polynomial expression, such as Equation 4 below.

$$\gamma = c_0 + c_1 \cdot x + c_2 \cdot x^2 + c_3 \cdot x^3 + \ldots + c_n \cdot x^n \quad \text{Equation 4}$$

The absorption function ($\gamma(x)$) for model B in FIG. 6 is a parabolic function that considers a parameter for carbohydrate total absorption time ($t_a$). The carbohydrate absorption function ($\gamma(x)$) for model B is shown in Equation 5 below.

$$\begin{cases} \gamma(x) = -\frac{1}{t_a^2} x^2 + \frac{2}{t_a} x & \text{if } 0 \leq x \leq t_a \\ \gamma(x) = 1 & \text{if } x > t_a \end{cases} \quad \text{Equation 5}$$

where:
$\gamma(x)$=Carbohydrate absorption function;
x=Time frame of interest (in minutes); and
$t_a$=Total carbohydrate absorption time.

Model C in FIG. 6 is a linear carbohydrate absorption function ($\gamma(x)$) as represented by Equation 6 below.

$$\begin{cases} \gamma(x) = \frac{1}{t_a} x & \text{if } 0 \leq x \leq t_a \\ \gamma(x) = 1 & \text{if } x > t_a \end{cases} \quad \text{Equation 6}$$

where:
$\gamma(x)$=Carbohydrate absorption function;
x=Time frame of interest (in minutes); and
$t_a$=Total carbohydrate absorption time.

Model D in FIG. 6 is an exponential carbohydrate absorption function ($\gamma(x)$) as represented by Equation 7 below.

$$\gamma(x) = 1 - e^{-a \cdot x} \quad \text{Equation 7}$$

where:
$\gamma(x)$=Carbohydrate absorption function;
x=Time frame of interest (in minutes); and
a=0.03.

Model E in FIG. 6 is a second exponential carbohydrate absorption function ($\gamma(x)$) as represented by Equation 8 below.

$$\gamma(x) = 1 - e^{-a \cdot x^2 - b \cdot x} \quad \text{Equation 8}$$

where:
$\gamma(x)$=Carbohydrate absorption function;
x=Time frame of interest (in minutes);
a=0.0004; and
b=0.015.

Returning to FIG. 5, based on the carbohydrate absorption function ($\gamma(x)$) used, the meter 104 is able to calculate the relative threshold ($BG_{end,relative}$) so as to determine whether the hypoglycemia has been properly addressed or if additional treatment (e.g., carbohydrate ingestion) is required. If a carbohydrate amount has been ingested only once since hypoglycemia detection, then the relative threshold ($BG_{end,relative}$) can be calculated using Equation 9 below.

$$BG_{end,relative} = \gamma(t-t_1) \cdot BG_{hypo,end} + (1-\gamma(t\ t_1)) \cdot BG_0 \qquad \text{Equation 9}$$

where:
$BG_{end,relative}$=Relative threshold for ending the surveillance phase;
$BG_{hypo,end}$=Threshold where hypoglycemia is considered ended;
$\gamma(x)$=Carbohydrate absorption function for time interval x;
t=Current time when relative threshold is being calculated;
$t_1$=Time when first carbohydrate recommended or consumed; and
$BG_0$=Original blood glucose measurement (i.e., when hypoglycemia was detected).

When carbohydrates have been ingested twice since hypoglycemia detection, then the relative threshold ($BG_{end,relative}$) can be calculated using Equation 10 below.

$$BG_{end,relative} = \gamma(t-t_2) \cdot BG_{hypo,end} + \qquad \text{Equation 10}$$
$$(1-\gamma(t-t_2)) \cdot BG_2 + \frac{\gamma(t-t_2)}{\gamma(t_2-t_1)}(\gamma(t-t_1)-1)(BG_2-BG_1)$$

where:
$BG_{end,relative}$=Relative threshold for ending the surveillance phase;
$BG_{hypo,end}$=Threshold where hypoglycemia is considered ended;
$\gamma(x)$=Carbohydrate absorption function for time interval x;
t=Current time when relative threshold is being calculated;
$t_n$=Time of $n^{th}$ measurement since hypoglycemia; and
$BG_n$=$n^{th}$ blood glucose measurement since hypoglycemia.

When three or more carbohydrate ingestion events occur since hypoglycemia detection, the relative threshold ($BG_{end,relative}$) is calculated by superimposing the effects of the multiple carbohydrate ingestions.

When hypoglycemia symptoms persist and/or the blood glucose levels are still not ideal, such as when the blood glucose measurements fail the end threshold ($BG_{hypo,end}$) and the relative threshold ($BG_{end,relative}$) tests, the meter 104 proceeds again to the carbohydrate computation phase 504. For the second and subsequent carbohydrate calculations in stage 504, the meter 104 considers previous blood glucose measurements along with previously recommended and/or consumed carbohydrate amounts. The rate of change in the blood glucose level can also be considered along with other factors, like the time difference between the measurements. As noted before, conventional methods for carbohydrate computation in case of hypoglycemia are based on a fixed threshold for blood glucose assessment and do not consider prior information. Questionable treatment recommendations can occur for example when blood glucose measurements are made too close together or fail to consider the amount of carbohydrates previously consumed by the patient. For instance, if the blood glucose increase following carbohydrate ingestion (e.g., blood glucose is measured after 15 minutes) is smaller than expected or even worse if blood glucose does not increase at all, then additional carbohydrates must be recommended whatever the carbohydrate absorption model. On the other hand ignoring previous carbohydrate ingestion and applying the same carbohydrate computation process at each blood glucose measurement can lead to an excess of carbohydrate ingested by the patient leading to poor glucose control.

For example, if the blood glucose level of the patient ($BG_1$) was initially 45 mg/dl, a conventional method would diagnose the patient as experiencing hypoglycemia because the blood glucose level was below the traditional 60 mg/dl threshold. Following the conventional protocol, the patient would be instructed to consume a first carbohydrate amount to counteract the hypoglycemia. Staying with this hypothetical, 15 minutes later a second blood glucose measurement ($BG_2$) of 55 mg/dl is measured. Using a conventional treatment protocol, given that this second blood glucose measurement ($BG_2$) is still below the 60 mg/dl limit, the patient would again be instructed to consume a second amount of carbohydrate. However, consuming this second carbohydrate amount might result in overshooting the target blood glucose range some minutes or a few hours later. This traditional approach failed to consider the 10 mg/dl increase between the first ($BG_1$) and second ($BG_2$) blood glucose readings. Based on this increase in the blood glucose level, it should be expected that the blood glucose level would continue to increase due to the initial carbohydrate ingestion, and the target blood glucose level might be possibly reached without any need of additional carbohydrate ingestion. The method described herein takes previous information (e.g., previous blood glucose measurements and carbohydrate ingestion) into account to compute in stage 504 additional carbohydrate amount recommendations more accurately.

Figure 7:
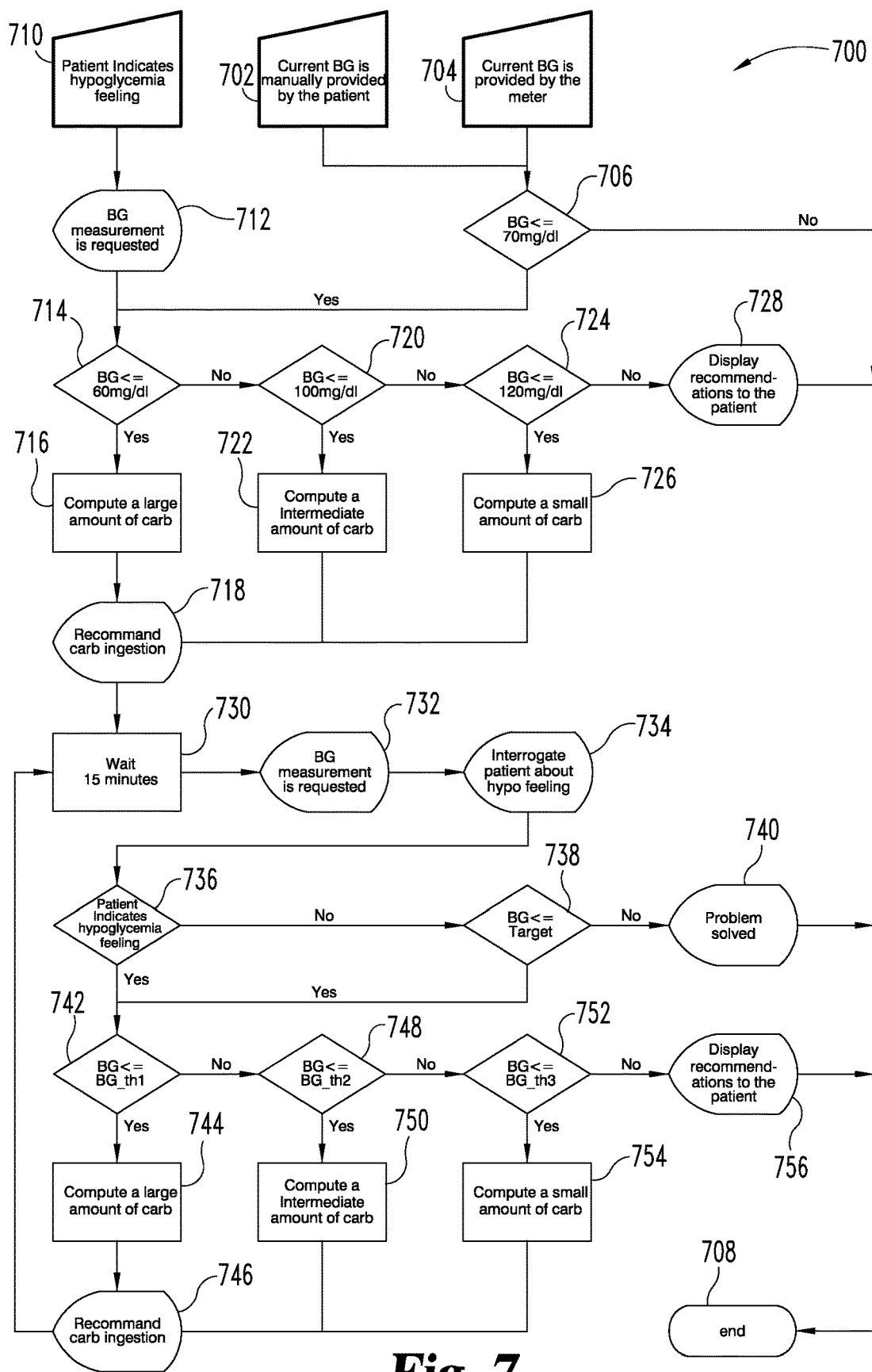
FIG. 7 is a flowchart showing a method for detecting and treating hypoglycemia, according to at least one embodiment of the present disclosure.

FIG. 7 is a flowchart 700 for one variation of the method for detecting and treating hypoglycemia, and FIG. 17, which will be discussed later, shows another variation of the method. Among other things, the methods illustrated by FIGS. 7 and 17 differ in how the carbohydrate computation occurs.

Figure 5:
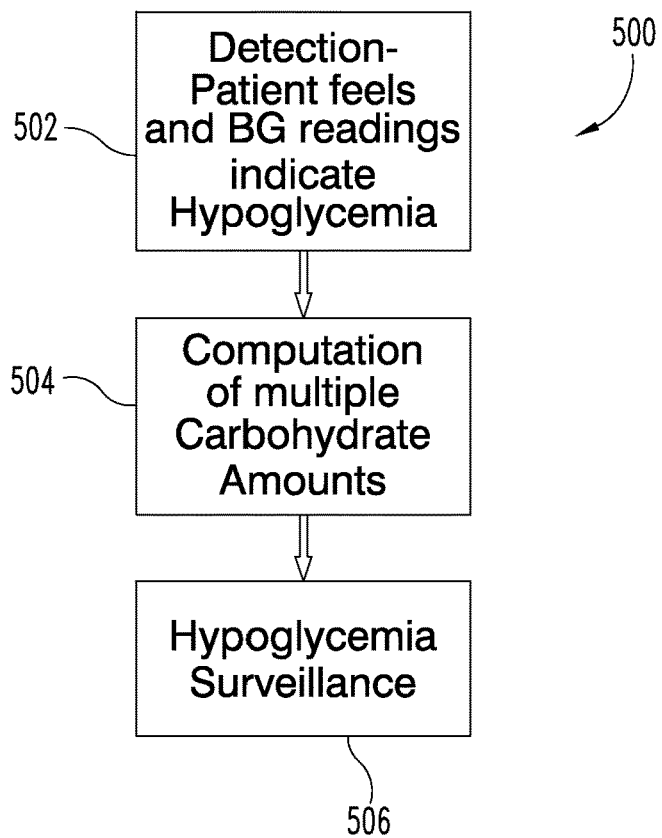
FIG. 5 is a flowchart showing the general phases of a method for detecting and treating hypoglycemia, according to at least one embodiment of the present disclosure.

As should be recognized, the method depicted by the flow chart 700 in FIG. 7 shares the same general phases as those previously described with respect to the flowchart 500 in FIG. 5. During the hypoglycemia detection phase 502, the current blood glucose measurement (BG) for the patient can be manually entered into the meter 104 in stage 702 or automatically entered into the meter 104 in stage 704. The meter 104 in stage 706 compares the current blood glucose reading (BG) to an established threshold for hypoglycemia ($BG_{hypo,detection}$). In the illustrated example, the threshold for hypoglycemia ($BG_{hypo,detection}$) is 70 mg/dl, but it should be recognized that this threshold can be different in other variations. When the current blood glucose reading (BG) is above the threshold for hypoglycemia ($BG_{hypo,detection}$), then no hypoglycemia is apparently occurring, and the meter 104 proceeds to stage 708 where the routine ends. Of course, the meter 104 at stage 708 can start over again monitoring for hypoglycemia (i.e., proceed back to stage 702, 704, etc.). On the other hand, when the current blood glucose reading (BG) is at or below the threshold for hypoglycemia ($BG_{hypo,detection}$), the meter 104 proceeds to the carbohydrate computation phase 504 so as to compute the first or initial carbohydrate amount ($n_{BU,1}$) to correct the hypoglycemia, if needed.

As noted before, the hypoglycemia detection phase 502 also includes a hypoglycemia symptom component. By considering whether the patient is feeling the initial symptoms of hypoglycemia allows the meter 104 to treat the hypoglycemia earlier than by relying on the blood glucose measurements alone. The patient can indicate feeling hypoglycemia symptoms in stage 710. In one example, the patient notifies the meter 104 that they are feeling the effects of hypoglycemia through the I/O device 206 (e.g., by pressing a dedicated button). Then the patient is requested to measure their current blood glucose level in stage 712. Note again that treatment of the hypoglycemia can be possibly recommended at blood glucose values much higher than blood glucose threshold mentioned previously.

After either determining the blood glucose level is at or below the threshold (stage 706) or the patient indicates a feeling of hypoglycemia (stage 712), the meter 104 proceeds to calculate the recommended carbohydrate amount to treat the hypoglycemia based on the current blood glucose level of the patient (phase 504 in FIG. 5). In this example, the carbohydrate amounts are divided into three levels, small ($n_{BU,small}$), medium ($n_{BU,medium}$), and large ($n_{BU,large}$). As noted before, the carbohydrate amounts are typically expressed in terms of bread units, and a bread unit is equivalent to 12 grams of bread. Equation 11 below shows how the carbohydrate amounts are calculated for these three levels.

$$\begin{cases} n_{BU,small} = f_n(n_{BU,TDD} + n_{BU,fainting}) \\ n_{BU,medium} = f_n(n_{BU,TDD} + n_{BU,fainting} + 1) \\ n_{BU,large} = f_n(n_{BU,TDD} + n_{BU,fainting} + 2) \end{cases} \quad \text{Equation 11}$$

where:
$n_{BU,small}$=Small amount of carbohydrate;
$n_{BU,medium}$=Medium amount of carbohydrate;
$n_{BU,large}$=Large amount of carbohydrate;
$f_n$=Normalization factor based on patient weight;
$n_{BU,fainting}$=Risk of fainting additional bread unit; and
$n_{BU,TDD}$=Additional bread unit recommended for patients with a total daily dose (TDD) of insulin ≤30 UI.

In equation 11 above, additional carbohydrate amounts are recommended for patients with a total daily dose (TDD) of insulin smaller or equal to 30 units of insulin. Equation 12 shows this adjustment of adding one additional bread unit for such a patient.

$$\begin{cases} n_{BU,TDD} = 1 & \text{if } TDD \leq 30 \ UI \\ n_{BU,TDD} = 0 & \text{otherwise} \end{cases} \quad \text{Equation 12}$$

Regarding equation 11, additional carbohydrate amounts are recommended for patients having a history of fainting during hypoglycemia. Equation 13 shows this adjustment of adding one additional bread unit when the patient has a fainting risk.

$$\begin{cases} n_{BU,fainting} = 1 & \text{for patients with a history of unconsciousness} \\ n_{BU,fainting} = 0 & \text{otherwise} \end{cases} \quad \text{Equation 13}$$

As noted before, the normalization factor ($f_n$) is used to adjust the recommended carbohydrate amount based on the weight of the patient. Equation 14 below represents how this factor is calculated.

$$f_n = \frac{M - 0.5 \cdot M_{OW}}{70} \quad \text{Equation 14}$$

where:
M=patient weight (kilograms); and
$M_{OW}$=patient overweight (kilograms).

Whether a patient is overweight depends on a number of factors, including the weight (M) and height (H) of the patient. Equation 15 below provides an example to determine the patient overweight factor ($M_{OW}$).

$$M_{OW} = \begin{cases} 0 & \text{if } M - H + 100 < 0 \\ M - H + 100 & \text{if } M - H + 100 \geq 0 \end{cases} \quad \text{Equation 15}$$

where:
H=Height of the patient (centimeters);
M=patient weight (kilograms); and
$M_{OW}$=patient overweight (kilograms).

It should be appreciated that the physician or other health care provider can adjust these recommended carbohydrate amounts so as to customize the amounts for the particular needs of the patient.

Looking again at FIG. 7, the meter 104 calculates the first amount of carbohydrate ($n_{BU,1}$) right after hypoglycemia is detected (at time $t_1$). The first amount of carbohydrate ($n_{BU,1}$) is obtained by comparing the first blood glucose measurement ($BG_1$), which was made during stages 706 or 712, with the very low ($BG_{vl,1}$), low ($BG_{l,1}$), and medium-low ($BG_{ml,1}$) blood glucose range limits. In one example, the very low ($BG_{vl,1}$), low ($BG_{l,1}$), and medium-low ($BG_{ml,1}$) blood glucose range limits are 60 mg/dl, 100 mg/dl, and 140 mg/di, respectively. However, these limits can be different in other examples. In for example the flowchart 700 in FIG. 7, the very low ($BG_{vl,1}$), low ($BG_{l,1}$), and medium-low ($BG_{ml,1}$) blood glucose range limits are respectively 60 mg/dl, 100 mg/dl, and 120 mg/dl. Equation 16 below shows how the first amount of carbohydrate ($n_{BU,1}$) is determined based on these glucose ranges limits.

$$n_{BU,1} = \begin{cases} 0 & \text{if } BG_{ml,1} < BG_1 \\ n_{BU,small} & \text{if } BG_{l,1} < BG_1 \leq BG_{ml,1} \\ n_{BU,medium} & \text{if } BG_{vl,1} < BG_1 \leq BG_{l,1} \\ n_{BU,large} & \text{if } BG_1 \leq BG_{vl,1} \end{cases} \quad \text{Equation 16}$$

where:
$n_{BU,1}$=First amount of carbohydrate computed right at hypoglycemia detection (i.e., at time $t_1$);
$n_{BU,small}$=Small amount of carbohydrate;
$n_{BU,medium}$=Medium amount of carbohydrate;
$n_{BU,large}$=Large amount of carbohydrate;
$BG_1$=Blood glucose measurement at hypoglycemia detection (i.e., at time $t_1$);
$BG_{ml,1}$=Medium-low blood glucose range limit or threshold for a first amount of carbohydrate (i.e., at time $t_1$);
$BG_{l,1}$=Low blood glucose range limit or threshold for a first amount of carbohydrate (i.e., at time $t_1$); and
$BG_{vl,1}$=Very low blood glucose range limit or threshold for a first amount of carbohydrate (i.e., at time $t_1$).

Figure 8:
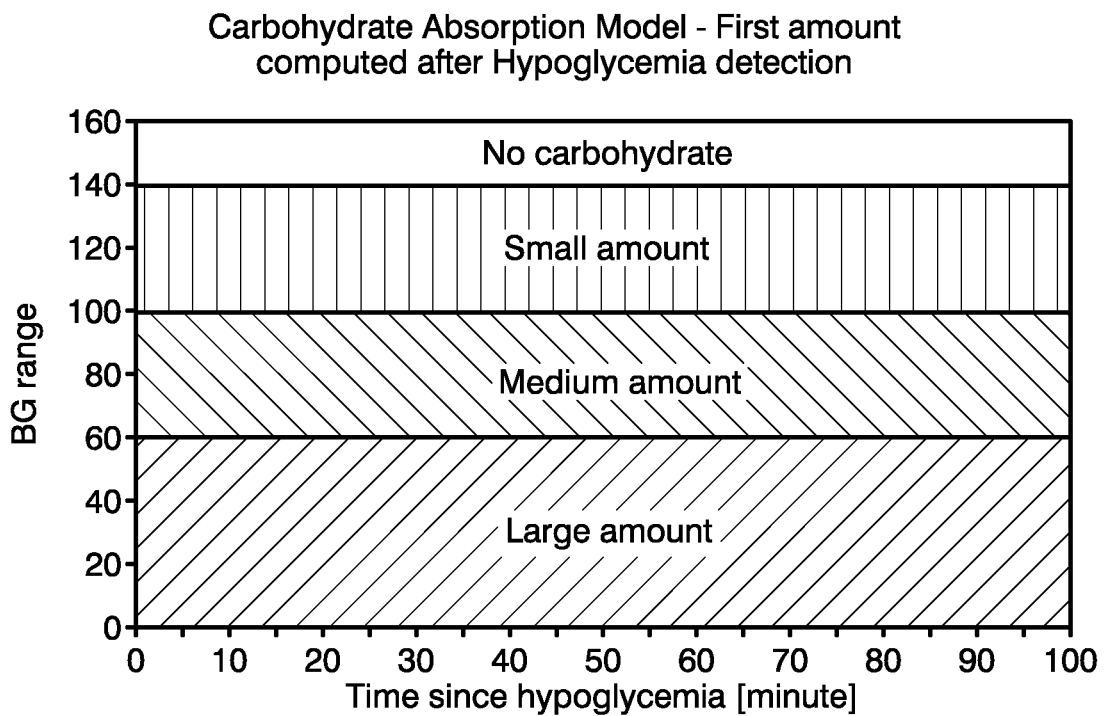
FIG. 8 is a graph displaying four blood glucose ranges used to compute a first amount of carbohydrates ($n_{BU,1}$) at hypoglycemia detection time ($t_1$)

It should be appreciated that the meter 104 determines the small ($n_{BU,small}$), medium ($n_{BU,medium}$), and large ($n_{BU,large}$) carbohydrate amounts based on the equations 11-15 as was discussed above. FIG. 8 illustrates how the first amount of carbohydrate is computed based on the first blood glucose reading ($BG_1$) taken at the time ($t_1$) when hypoglycemia was first detected. Since at this stage no previous carbohydrates were consumed close to the hypoglycemia event, the ranges separating the various carbohydrate amounts are constant over time, because the model does not include increases due to any carbohydrate absorption. In other words, recommended ranges for the small ($n_{BU,small}$), medium ($n_{BU,medium}$), and large ($n_{BU,large}$) carbohydrate amounts (as well as no carbohydrates) are constant over time for the initial calculation. For example, when the first blood glucose reading ($BG_1$) is 80 mg/dl, the recommended medium carbohydrate amount ($n_{BU,medium}$) is the same at 25 and 55 minutes after detection of the hypoglycemia.

Looking now at stage 714 in FIG. 7, the meter 104 determines whether the first blood glucose measurement ($BG_1$) was at or below the very low ($BG_{vl,1}$) blood glucose limit, which in this example is 60 mg/dl. When the first blood glucose measurement ($BG_1$) is at or below this limit, the meter 104 calculates the large carbohydrate amount ($n_{BU,large}$) needed to be ingested by the patient based on equations 11-15. It should be recognized that lower blood glucose levels typically require higher amounts of carbohydrates be ingested in order to address hypoglycemia as compared to higher blood glucose levels. Once the large carbohydrate amount ($n_{BU,large}$) is calculated in stage 716, the meter 104 via the I/O device 206 provides to the patient and/or the health care provider the recommended large carbohydrate amount ($n_{BU,large}$) to ingest in stage 718. For example, the meter 104 can display to the patient that the patient should consume 3 bread units of carbohydrates to address the current condition.

When the first blood glucose measurement ($BG_1$) is greater than the very low ($BG_{vl,1}$) blood glucose limit, the meter 104 in stage 720 determines if the first blood glucose measurement ($BG_1$) is less than or equal to the low blood glucose limit ($BG_{l,1}$), which in FIG. 7 is 100 mg/dl. If the first blood glucose measurement ($BG_1$) is at or below this limit, the meter 104 calculates in stage 722 the medium or intermediate carbohydrate amount ($n_{BU,medium}$) needed to be ingested by the patient based on equations 11-15. Once the medium carbohydrate amount ($n_{BU,medium}$) is calculated in stage 722, the meter 104 via the I/O device 206 provides to the patient and/or the health care provider the recommended medium carbohydrate amount ($n_{BU,medium}$) to ingest in stage 718. For instance, the meter 104 can display to the patient that the patient should consume 2 bread units of carbohydrates to address the current situation.

In stage 720, if the first blood glucose measurement ($BG_1$) is greater than the low ($BG_{l,1}$) blood glucose limit, the meter 104 proceeds to stage 724 to determine if the first blood glucose measurement ($BG_1$) is less than or equal to the medium-low ($BG_{ml,1}$) blood glucose range limit, which in the illustrated example is 120 mg/dl. If the first blood glucose measurement ($BG_1$) is at or below this limit, the meter 104 calculates in stage 726 the small carbohydrate amount ($n_{BU,small}$) needed to be ingested by the patient. Once the small carbohydrate amount ($n_{BU,small}$) is calculated in stage 726, the meter 104 via the I/O device 206 provides to the patient and/or the health care provider the recommended medium carbohydrate amount ($n_{BU,medium}$) to ingest in stage 718. For instance, the meter 104 can display to the patient that the patient should consume 1 bread unit of carbohydrates to address the current situation. When the first blood glucose measurement ($BG_1$) is greater than the medium-low blood glucose range limit ($BG_{ml,1}$), the meter proceeds to stage 728 and displays any recommendations (or none at all) via the I/O device 206, and the analysis ends in stage 708.

After instructing the patient to ingest a particular amount of carbohydrates in stage 718, the meter 104 proceeds to the surveillance phase 506. As discussed before, upon ingesting the blood glucose level does not instantaneously rise. Instead, after the first carbohydrate amount is ingested, the blood glucose level is expected to gradually increase to the target, end of surveillance threshold ($BG_{hypo,end}$). If the second blood glucose reading ($BG_2$) is taken too close to the first measurement ($BG_1$), the analysis on whether the hypoglycemia has been addressed can be inaccurate. To address this issue, the method includes a delay between measurements in stage 730. In the illustrated example, the delay is 15 minutes, but it can be different in other examples (e.g., 10 or 20 minutes). After the delay, the meter 104 in stage 732 instructs the patient to perform a second blood glucose test so as to collect a second blood glucose reading ($BG_2$) or the meter 104 automatically performs the test. The meter 104 also asks the patient via the I/O device 206 whether the patient is feeling any symptoms associated with hypoglycemia in stage 734.

In stage 736, the meter 104 evaluates whether the patient indicated having a feeling of hypoglycemia. When there is no feeling or symptoms of hypoglycemia, the meter proceeds to stage 738 so as to evaluate the second blood glucose measurement ($BG_2$) against a target level for determining whether the surveillance phase 506 needs to continue. Equation 1 above provides an example of how the end of surveillance threshold ($BG_{hypo,end}$) is evaluated in stage 738. When the meter 104 determines the second blood glucose reading ($BG_2$) is above this target or end of surveillance threshold ($BG_{hypo,end}$), the meter 104 considers the hypoglycemia problem to be solved in stage 740 and can indicate as such via the I/O device 206. With the hypoglycemia problem solved, the meter 104 proceeds to end the analysis in stage 708.

On the other hand, when a patient indicates as having symptoms of hypoglycemia in stage 736 or the second blood glucose reading ($BG_2$) is not above the end of surveillance threshold ($BG_{hypo,end}$) in stage 738, the meter 104 then computes a second amount of carbohydrate to ingest starting in stage 742. Additional carbohydrates are recommended if the blood glucose level has not increased enough after the first carbohydrate ingestion. When the single, first amount of carbohydrate ($n_{BU,1}$) was already ingested, the second very low ($BG_{vl,2}$), second low ($BG_{l,2}$), and second medium-low ($BG_{ml,2}$) blood glucose range limits used to calculate the new, second amount of carbohydrate ($n_{BU,2}$) can possibly be different from the first very low ($BG_{vl,1}$), first low ($BG_{l,1}$), and first medium-low ($BG_{ml,1}$) blood glucose limits. At second measurement time ($t_2$), the second very low ($BG_{vl,2}$), second low ($BG_{l,2}$), and second medium-low ($BG_{ml,2}$) blood glucose limits depend upon the first (BG1) and second ($BG_2$) blood glucose measurements as well as the time elapsed since the previous carbohydrate ingestion ($\Delta t_{2,1} = t_2 - t_1$). Equation 17 shows an example of how these second limits are calculated.

$$\begin{cases} BG_{vl,2} = \gamma(t-t_1) \cdot BG_{vl,1} + (1 - \gamma(t-t_1)) \cdot BG_1 \\ BG_{l,2} = \gamma(t-t_1) \cdot BG_{l,1} + (1 - \gamma(t-t_1)) \cdot BG_1 \\ BG_{ml,2} = \gamma(t-t_1) \cdot BG_{ml,1} + (1 - \gamma(t-t_1)) \cdot BG_1 \end{cases} \quad \text{Equation 17}$$

where:
$BG_{vl,2}$=Very low blood glucose range limit or threshold for a second amount of carbohydrate (i.e., at time $t_2$);

$BG_{l,2}$=Low blood glucose range limit or threshold for a second amount of carbohydrate (i.e., at time $t_2$);

$BG_{ml,2}$=Medium-low blood glucose range limit or threshold for a second amount of carbohydrate (i.e., at time $t_2$);

$\gamma(x)$=Carbohydrate absorption function for time interval x;

t=Current time when relative threshold is being calculated;

$t_1$=Time when first carbohydrate was consumed; and $BG_1$=First blood glucose measurement (i.e., when hypoglycemia was detected).

Based on the limits calculated in equation 17 above, the second amount of carbohydrate $n_{BU,2}$ to ingest can be calculated through equation 18.

$$n_{BU,1} = \begin{cases} 0 & \text{if } BG_{ml,2} < BG_2 \\ n_{BU,small} & \text{if } BG_{l,2} < BG_2 \leq BG_{ml,2} \\ n_{BU,medium} & \text{if } BG_{vl,2} < BG_2 \leq BG_{l,2} \\ n_{BU,large} & \text{if } BG_2 \leq BG_{vl,2} \end{cases} \quad \text{Equation 18}$$

where:

$n_{BU,2}$=Second amount of carbohydrate to ingest (i.e., at time $t_2$);

$n_{BU,small}$=Small amount of carbohydrate;

$n_{BU,medium}$=Medium amount of carbohydrate;

$n_{BU,large}$=Large amount of carbohydrate;

$BG_2$=Second blood glucose measurement (i.e., at time $t_2$);

Again, it should be appreciated that the meter 104 determines the small ($n_{BU,small}$), medium ($n_{BU,medium}$), and large ($n_{BU,large}$) carbohydrate amounts based on the equations 11-15 as was discussed above. Of course, the physician or other health care provider can adjust these recommended carbohydrate amounts so as to customize the amounts for the particular needs of the patient.

FIGS. 9, 10, 11, and 12 illustrate how the second carbohydrate amounts are determined with different absorption models having different initial conditions. In these graphs, the second amount of carbohydrate ($n_{BU,2}$) depends on the first ($BG_1$) and second ($BG_2$) blood glucose measurements respectively obtained at the first measurement time ($t_1$) when hypoglycemia was detected and the current, second measurement time ($t_2$).

Figure 9:
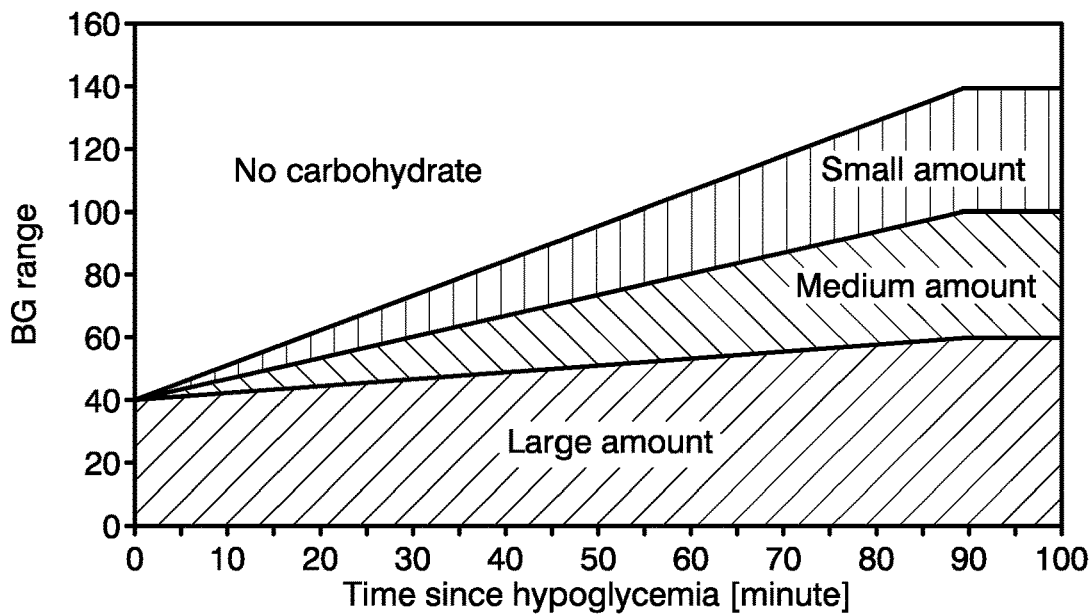
FIG. 9 is a graph displaying four ranges referring to a second blood glucose measurement ($BG_2$) used to compute a second amount of carbohydrates ($n_{BU,2}$) in relation to time since the hypoglycemia using a linear function when the first hypoglycemic blood glucose reading ($BG_1$) was 40 mg/dL.
Figure 10:
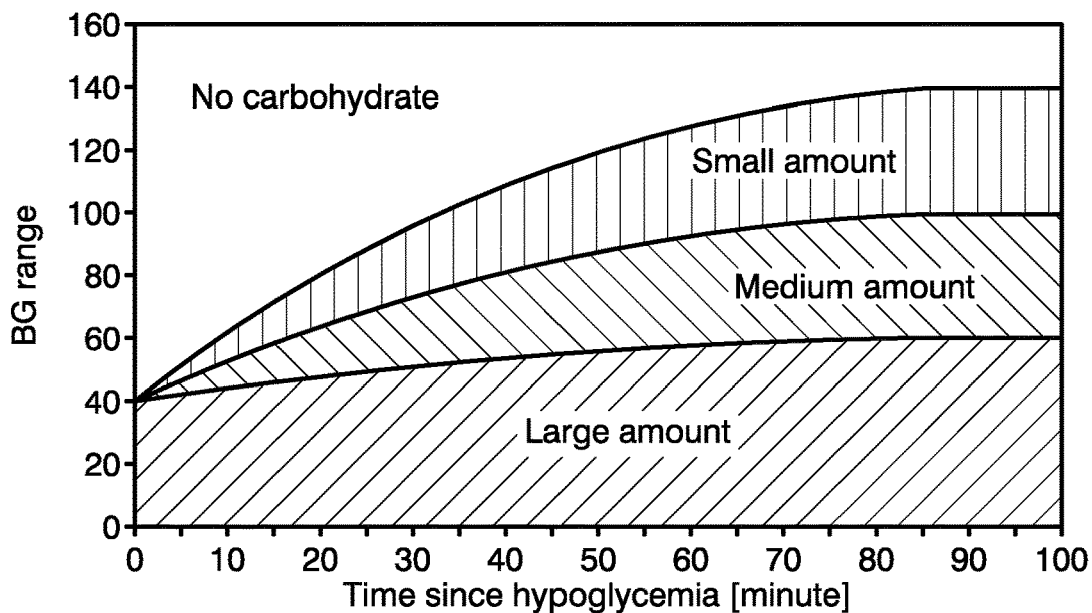
FIG. 10 is a graph displaying four ranges referring to the second blood glucose measurement ($BG_2$) used to compute the second amount of carbohydrates ($n_{BU,2}$) in relation to time since the hypoglycemia using a parabolic function when the first hypoglycemic blood glucose reading ($BG_1$) was 40 mg/dL.

Looking at FIGS. 9 and 10, both are graphs of four ranges of the second blood glucose measurement ($BG_2$) displayed as a function of time since the hypoglycemic event (t). In both graphs of FIGS. 9 and 10, the first blood glucose value ($BG_1$) was 40 mg/dl (at $t_1$=0). The first very low ($BG_{vl,1}$), first low ($BG_{l,1}$), and first medium-low ($BG_{ml,1}$) blood glucose limits in both examples respectively equal 60, 100, and 140 mg/dl. As can be seen in both graphs, the second very low ($BG_{vl,2}$), second low ($BG_{l,2}$), and second medium-low ($BG_{ml,2}$) blood glucose limits all are initially equal to 40 mg/dl and then slowly increase to the 60, 100, and 140 mg/dl limits in a 90 minute time window ($t_a$) following the initial ingestion of the first carbohydrate amount when the hypoglycemia was first detected. The carbohydrate absorption function ($\gamma(x)$) in FIG. 9 is based on linear absorption model C as was formulated in equation 6 above and illustrated in FIG. 6. In contrast, the carbohydrate absorption function ($\gamma(x)$) in FIG. 10 is based on parabolic absorption model B as was formulated in equation 5 above and illustrated in FIG. 6. As can be seen in both graphs, the second carbohydrate amount ($n_{BU,2}$) is smaller or even zero when the second blood glucose measurement ($BG_2$) is considerably higher than the first, 40 mg/dl measurement ($BG_1$). For example, when the second blood glucose measurement ($BG_2$) in FIG. 9 is 80 mg/dl 15 minutes after the hypoglycemia being detected, no carbohydrates are required.

Figure 11:
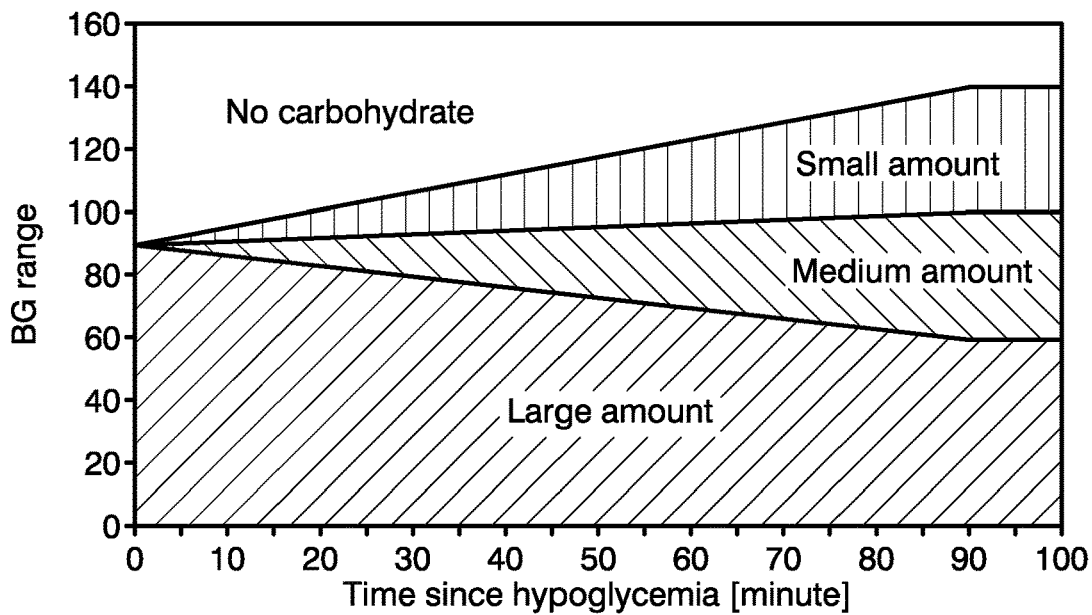
FIG. 11 is a graph displaying four ranges referring to the second blood glucose measurement ($BG_2$) used to compute a second amount of carbohydrates ($n_{BU,2}$) in relation to time since the hypoglycemia using a linear function when the first hypoglycemic blood glucose reading ($BG_1$) was 90 mg/dL.
Figure 12:
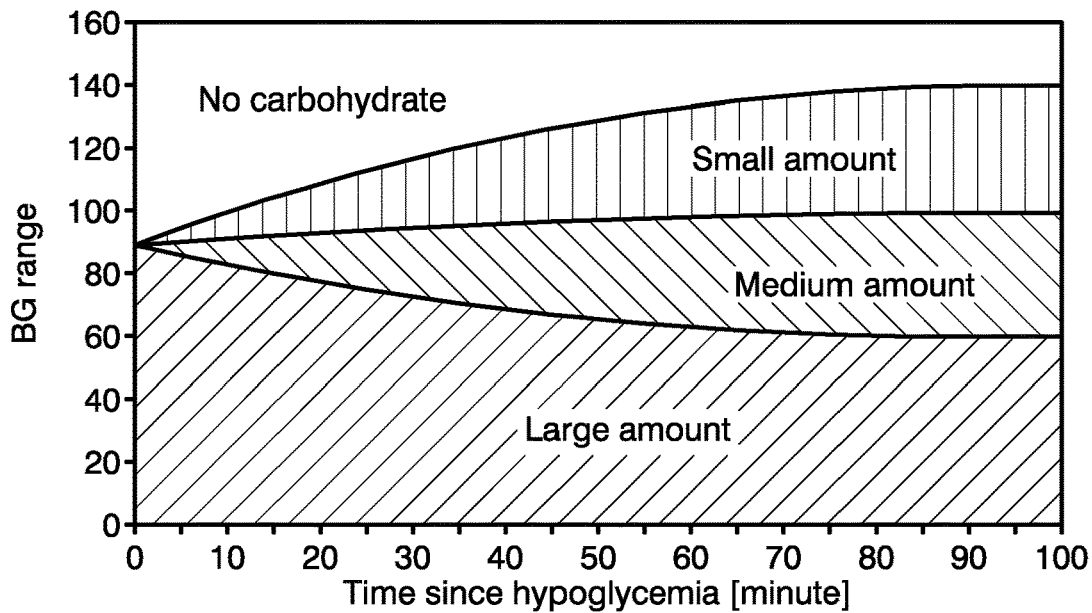
FIG. 12 is a graph displaying four ranges referring to the second blood glucose measurement ($BG_2$) used to compute the second amount of carbohydrates ($n_{BU,2}$) in relation to time since the hypoglycemia using a parabolic function when the first hypoglycemic blood glucose reading ($BG_1$) was 90 mg/dL.

The graph FIG. 11 is similar to the graph in FIG. 9 in that the carbohydrate absorption function ($\gamma(x)$) in FIG. 11 is based on the same linear absorption model C as was formulated in equation 6 above. The graph in FIG. 12 is similar to the graph in FIG. 10 by that the carbohydrate absorption function ($\gamma(x)$) in FIG. 12 is based on the same parabolic absorption model B as was formulated in equation 5 above. However, the graphs in FIGS. 11 and 12 differ from those in FIGS. 9 and 10 by the fact that the first blood glucose measurement ($BG_1$) in FIGS. 11 and 12 are 90 mg/dl, rather than the 40 mg/dl first blood glucose measurement in FIGS. 9 and 10. Like before, the first very low ($BG_{vl,1}$), first low ($BG_{l,1}$), and first medium-low ($BG_{ml,1}$) blood glucose limits in FIGS. 11 and 12 respectively equal 60, 100, and 140 mg/dl. As can be seen in both graphs, the second very low ($BG_{vl,2}$), second low ($BG_{l,2}$), and second medium-low ($BG_{ml,2}$) blood glucose limits all are initially equal to 40 mg/dl and then slowly increase to the 60, 100, and 140 mg/dl limits in a 90 minute time window ($t_a$).

Referring again to FIG. 7, when a patient indicates having symptoms of hypoglycemia in stage 736 or the second blood glucose reading ($BG_2$) is not above the end of surveillance threshold ($BG_{hypo,end}$) in stage 738, the meter 104 then computes a second amount of carbohydrate to ingest (phase 504). In stage 742, the meter 104 determines whether the second blood glucose measurement ($BG_2$) was less than or equal to the second very low ($BG_{vl,2}$) blood glucose limit as was calculated in the manner previously discussed (see, equation 17). When the second blood glucose measurement ($BG_2$) is at or below this limit, the meter 104 calculates the large carbohydrate amount ($n_{BU,large}$) needed to be ingested by the patient in stage 744 based on equations 11-15. Once the large carbohydrate amount ($n_{BU,large}$) is calculated in stage 744, the meter 104 via the I/O device 206 provides to the patient and/or the health care provider the recommended large carbohydrate amount ($n_{BU,large}$) to ingest in stage 746. For example, the meter 104 can display to the patient that the patient should consume 3 bread units of carbohydrates to address the current condition.

When the second blood glucose measurement ($BG_2$) is greater than the second very low ($BG_{vl,2}$) blood glucose limit, the meter 104 in stage 748 determines if the second blood glucose measurement ($BG_2$) is less than or equal to the low blood glucose limit ($BG_{l,1}$), which in FIG. 7 is 100 mg/dl. If the second blood glucose measurement ($BG_2$) is at or below this limit, the meter 104 calculates in stage 750 the medium or intermediate carbohydrate amount ($n_{BU,medium}$) needed to be ingested. Once the medium carbohydrate amount ($n_{BU,medium}$) is calculated in stage 750, the meter 104 via the I/O device 206 provides to the patient and/or the health care provider the recommended medium carbohydrate amount (to ingest in stage 746. For instance, the meter 104 can display to the patient that the patient should consume 2 bread units of carbohydrates to address the current situation.

If in stage 748 the second blood glucose measurement ($BG_2$) is greater than the second low ($BG_{l,2}$) blood glucose limit, the meter 104 proceeds to stage 752 to determine if the second blood glucose measurement ($BG_2$) is less than or equal to medium-low ($BG_{ml,1}$) blood glucose range limit. If the second blood glucose measurement ($BG_2$) is at or below this limit, the meter 104 calculates in stage 754 the small carbohydrate amount ($n_{BU,small}$) needed to be ingested by the patient. Once the small carbohydrate amount ($n_{BU,small}$) is calculated in stage 754, the meter 104 via the I/O device 206 provides to the patient and/or the health care provider the recommended medium carbohydrate amount ($n_{BU,medium}$) to ingest in stage 746. For instance, the meter 104 can display to the patient that the patient should consume 1 bread unit of carbohydrates to address the current situation. It should be noted that the blood glucose values ("BG") and threshold limits ("BG_th1", "BG_th2", "BG_th3") are referenced in a generic sense in stages 742, 748, and 752, because the method may require the calculation of additional carbohydrate amounts over more than two carbohydrate amounts.

As noted before with respect to equation 2, the surveillance phase 506 can end when the blood glucose reading (BG) exceeds a second, relative threshold ($BG_{end,relative}$) that varies depending on the amount of carbohydrates previously consumed. For instance in the flowchart 700 of FIG. 7, when the second blood glucose measurement ($BG_2$) is greater than the second medium-low blood glucose range limit ($BG_{ml,2}$), the meter proceeds to stage 756 and displays any recommendations (or none at all) via the I/O device 206, and the analysis ends in stage 708.

After instructing the patient to ingest a particular amount of carbohydrates in stage 746, the meter 104 continues with the surveillance phase 502 by proceeding to the test delay stage 730. At that point, the surveillance and carbohydrate amount computations can continue for 3 or even more measurements and carbohydrate amounts until the hypoglycemia is remedied.

To compute a third amount of carbohydrate ($n_{BU,3}$), the current, third blood glucose reading ($BG_3$) is considered along with the previous measurements ($BG_1$ and $BG_2$). Specifically, at the third measurement time ($t_3$), the third very low ($BG_{vl,3}$), third low ($BG_{l,3}$), and third medium-low ($BG_{ml,3}$) blood glucose limits depend upon the first ($BG_1$) and second ($BG_2$) blood glucose measurements as well as the time elapsed. The third very low ($BG_{vl,3}$), third low ($BG_{l,3}$), and third medium-low ($BG_{ml,3}$) blood glucose limits are generally obtained by superimposing the effect of the first ($n_{BU,1}$) and second ($n_{BU,2}$) carbohydrate amounts on patient blood glucose concentration. Equation 19 below shows an example of how these third limits are calculated (see also, equation 10).

$$\begin{cases} BG_{vl,3} = \gamma(t-t_2)\cdot BG_{vl,3} + (1-\gamma(t-t_2))\cdot BG_2 + \dfrac{\gamma(t-t_2)}{\gamma(t_2-t_1)}(\gamma(t-t_1)-1)(BG_2-BG_1) \\ BG_{l,3} = \gamma(t-t_2)\cdot BG_{l,3} + (1-\gamma(t-t_2))\cdot BG_2 + \dfrac{\gamma(t-t_2)}{\gamma(t_2-t_1)}(\gamma(t-t_1)-1)(BG_2-BG_1) \\ BG_{ml,3} = \gamma(t-t_2)\cdot BG_{ml,3} + (1-\gamma(t-t_2))\cdot BG_2 + \dfrac{\gamma(t-t_2)}{\gamma(t_2-t_1)}(\gamma(t-t_1)-1)(BG_2-BG_1) \end{cases}$$ Equation 19 where:
$BG_{vl,3}$=Very low blood glucose range limit or threshold for a third amount of carbohydrate (i.e., at time t3);
$BG_{l,3}$=Low blood glucose range limit or threshold for a third amount of carbohydrate (i.e., at time t3);
$BG_{ml,3}$=Medium-low blood glucose range limit or threshold for a third amount of carbohydrate (i.e., at time t3);
$\gamma(x)$=Carbohydrate absorption function for time interval x;
t=Current time when relative threshold is being calculated;
$t_n$=Time of $n^{th}$ measurement since hypoglycemia; and
$BG_n$=$n^{th}$ blood glucose measurement since hypoglycemia.

Based on the limits calculated in equation 19 above, the third amount of carbohydrate ($n_{BU,3}$) to ingest can be calculated through equation 20.

$$n_{BU,1} = \begin{cases} 0 & \text{if } BG_{ml,3} < BG_3 \\ n_{BU,small} & \text{if } BG_{l,3} < BG_3 \le BG_{ml,3} \\ n_{BU,medium} & \text{if } BG_{vl,3} < BG_3 \le BG_{l,3} \\ n_{BU,large} & \text{if } BG_3 \le BG_{vl,3} \end{cases}$$ Equation 20 where:
$n_{BU,3}$=Third amount of carbohydrate to ingest (i.e., at time $t_3$);
$n_{BU,small}$=Small amount of carbohydrate;
$n_{BU,medium}$=Medium amount of carbohydrate;
$n_{BU,large}$=Large amount of carbohydrate;
$BG_3$=Third blood glucose measurement (i.e., at time $t_3$);

Again, it should be appreciated that the meter 104 determines the small ($n_{BU,small}$), medium ($n_{BU,medium}$), and large ($n_{BU,large}$) carbohydrate amounts based on the equations 11-15 as was discussed above. Of course, the physician or other health care provider can adjust these recommended carbohydrate amounts so as to customize the amounts for the particular needs of the patient.

FIGS. 13, 14, 15, and 16 illustrate how the third carbohydrate amounts are determined with different absorption models having different initial conditions. In these graphs, the third of amount carbohydrate ($n_{BU,3}$) depends on the first ($BG_1$), second ($BG_2$), and third second ($BG_3$) blood glucose measurements respectively obtained at the first measurement time ($t_1$) when hypoglycemia was detected, the second measurement time ($t_2$), and the third measurement time ($t_3$). It should be noted that in these graphs the time scale starts at the second measurement time ($t_2$), which in this example is 15 minutes after hypoglycemia detection.

Figure 13:
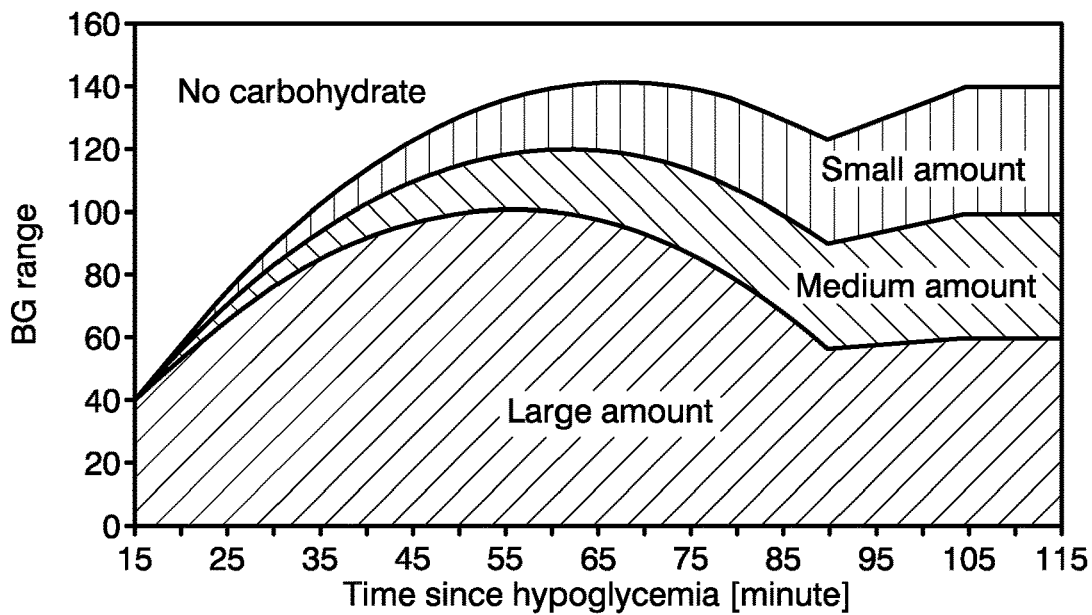
FIG. 13 is a graph displaying four ranges referring to a third blood glucose measurement ($BG_3$) used to compute a third amount of carbohydrates ($n_{BU,3}$) in relation to time since the hypoglycemia using a linear function when the first hypoglycemic blood glucose reading ($BG_1$) was 90 mg/dL and the second blood glucose reading ($BG_2$) was 40 mg/dL.
Figure 14:
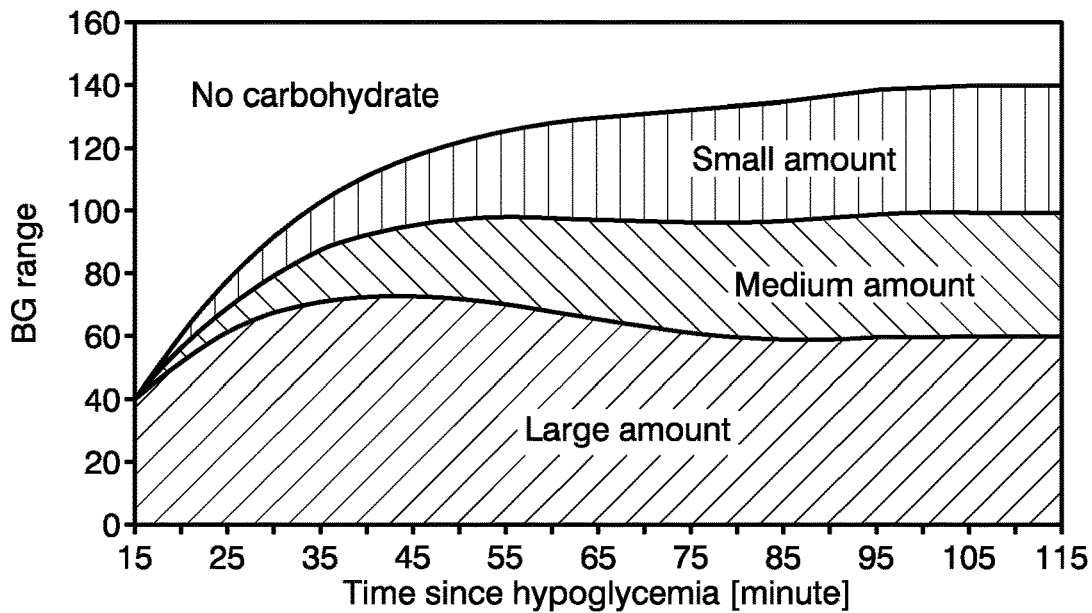
FIG. 14 is a graph displaying four ranges referring to the third blood glucose measurement ($BG_3$) used to compute the third amount of carbohydrates ($n_{BU,3}$) in relation to time since the hypoglycemia using a parabolic function when the first hypoglycemic blood glucose reading ($BG_1$) was 90 mg/dL and the second blood glucose reading ($BG_2$) was 40 mg/dL.

In FIGS. 13 and 14, the first blood glucose measurement ($BG_1$) was 90 mg/dl, and the second blood glucose measurement ($BG_2$) was 40 mg/dl. The third very low ($BG_{vl,3}$), low ($BG_{l,3}$), and medium-low ($BG_{ml,3}$) blood glucose limits in both graphs are plotted as a function of time ($t=t_3-t_1$) with the first very low ($BG_{vl,1}$), low ($BG_{l,1}$), and medium-low ($BG_{ml,1}$) blood glucose limits respectively equal 60, 100, and 140 mg/dl. The carbohydrate absorption function ($\gamma(x)$) for the third carbohydrate amount in FIG. 13 is based on linear absorption model C as was formulated in equation 6 above and illustrated in FIG. 6. In contrast, the carbohydrate absorption function ($\gamma(x)$) for the third carbohydrate amount in FIG. 14 is based on parabolic absorption model B as was formulated in equation 5 above and illustrated in FIG. 6. As can be seen, the third very low ($BG_{vl,3}$), low ($BG_{l,3}$), and medium-low ($BG_{ml,3}$) blood glucose limits in FIGS. 13 and 14 are initially equal to 40 mg/dl and increase much faster toward the limits as compared to those shown in FIGS. 9 and 10. This is due to the negative difference between the first ($BG_2$) and second ($BG_1$) blood glucose measurements which in turn shows that the first carbohydrate amount ($n_{BU,1}$) was too small to bring the blood glucose level back into the control range. As a result, a more aggressive pattern for addressing the hypoglycemia is proposed in order to compute larger amounts of carbohydrates.

Figure 15:
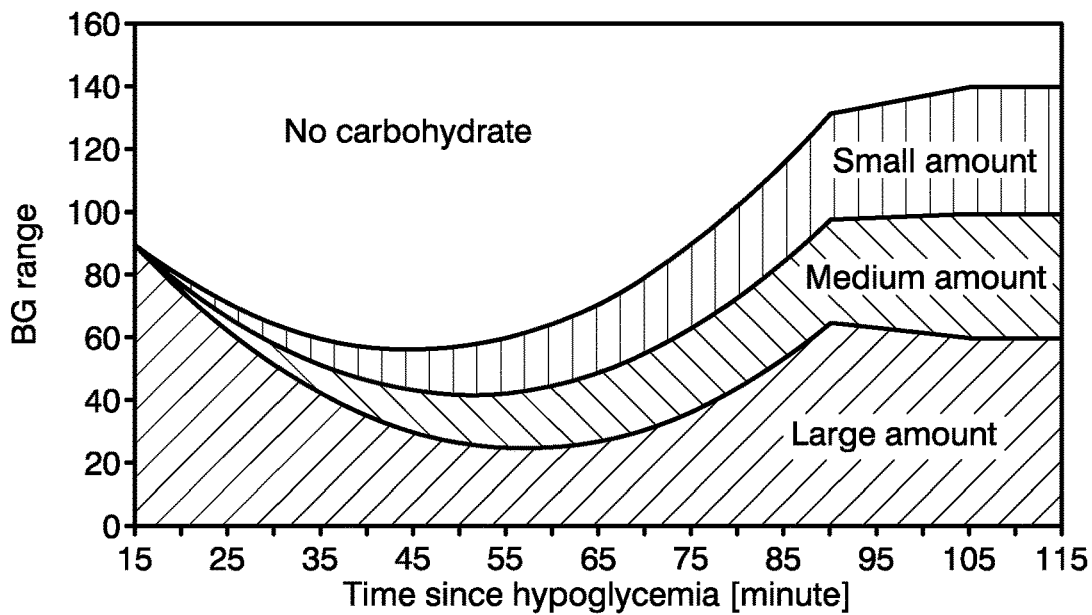
FIG. 15 is a graph displaying four ranges referring to a third blood glucose measurement ($BG_3$) used to compute a third amount of carbohydrates ($n_{BU,3}$) in relation to time since the hypoglycemia using a linear function when the first hypoglycemic blood glucose reading ($BG_1$) was 40 mg/dL and the second blood glucose reading ($BG_2$) was 90 mg/dL.
Figure 16:
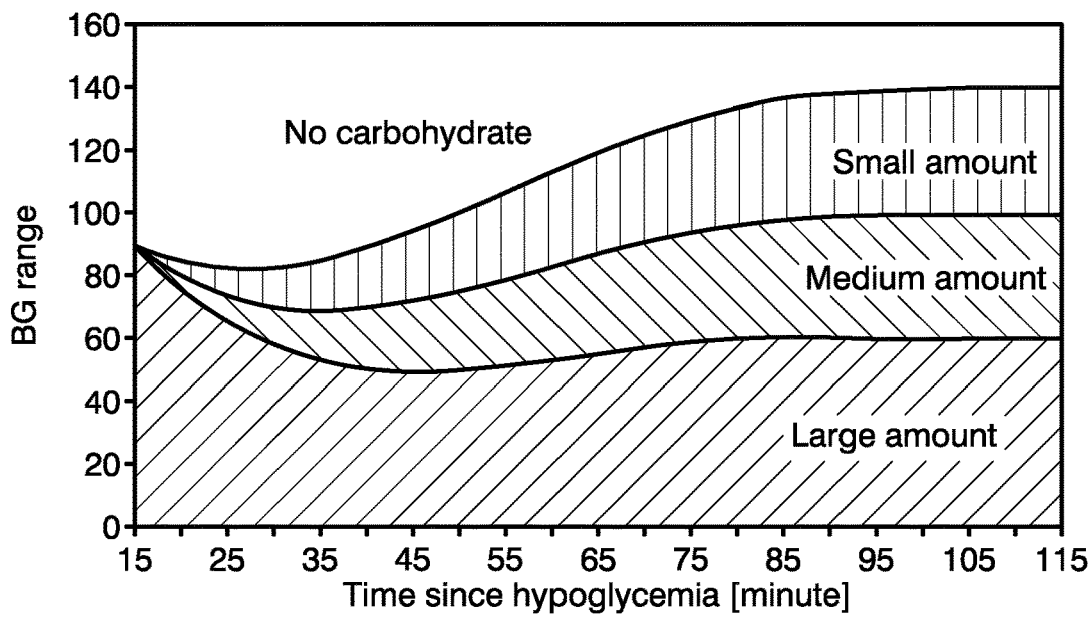
FIG. 16 is a graph displaying four ranges referring to the third blood glucose measurement ($BG_3$) used to compute the third amount of carbohydrates ($n_{BU,3}$) in relation to time since the hypoglycemia using a parabolic function when the first hypoglycemic blood glucose reading ($BG_1$) was 40 mg/dL and the second blood glucose reading ($BG_2$) was 90 mg/dL.

In FIGS. 15 and 16, the first blood glucose measurement ($BG_1$) was 40 mg/dl, and the second blood glucose measurement ($BG_2$) was 90 mg/dl. The third very low ($BG_{vl,3}$), low ($BG_{l,3}$), and medium-low ($BG_{ml,3}$) blood glucose limits in both graphs are plotted as a function of time ($t=t_3-t_1$) with the first very low ($BG_{vl,1}$), low ($BG_{l,1}$), and medium-low ($BG_{ml,1}$) blood glucose limits respectively equal 60, 100, and 140 mg/dl. The carbohydrate absorption function ($\gamma(x)$) for the third carbohydrate amount in FIG. 15 is based on linear absorption model C, and the carbohydrate absorption function ($\gamma(x)$) for the third carbohydrate amount in FIG. 16 is based on parabolic absorption model B. As can be seen, the third very low ($BG_{vl,3}$), low ($BG_{l,3}$), and medium-low ($BG_{ml,3}$) blood glucose limits in both FIGS. 15 and 16 are initially equal to 90 mg/dl at the second measurement time ($t_2$), and they tend to initially decrease before approaching the 60, 100, and 140 mg/dl limit values. This is due to the large positive difference between the first ($BG_2$) and second ($BG_1$) blood glucose measurements which in turn shows that the first carbohydrate amount ($n_{BU,1}$) was effective in bringing the blood glucose level back into the control range. As a result, a less aggressive approach for addressing the hypoglycemia is proposed in this situation in which smaller amounts of carbohydrates are recommended.

As noted before, this method can be used to calculate carbohydrate amounts ($n_{BU}$) even after three recommendations for ingesting carbohydrates. If three or more ingestions of carbohydrates occur after detecting hypoglycemia, the very low ($BG_{vl}$), low ($BG_l$), and medium-low ($BG_{ml}$) blood glucose limits or thresholds are obtained by superimposing the effects of the previous carbohydrate amounts. In this situation, the carbohydrate amount ($n_{BU}$) can be generically characterized by equation 21 below.

$$n_{BU,1} = \begin{cases} 0 & \text{if } BG_{ml} < BG \\ n_{BU,small} & \text{if } BG_l < BG \leq BG_{ml} \\ n_{BU,medium} & \text{if } BG_{vl} < BG \leq BG_l \\ n_{BU,large} & \text{if } BG \leq BG_{vl} \end{cases} \quad \text{Equation 21}$$

In a further variation, to simplify the calculation of the very low ($BG_{vl}$), low ($BG_l$), and medium-low ($BG_{ml}$) blood glucose limits, only three or even two of the last blood glucose measurements, including the current blood glucose measurement, are used. In this situation, all previous measurements would be considered, but the carbohydrate ingestion would be ignored.

Figure 17:
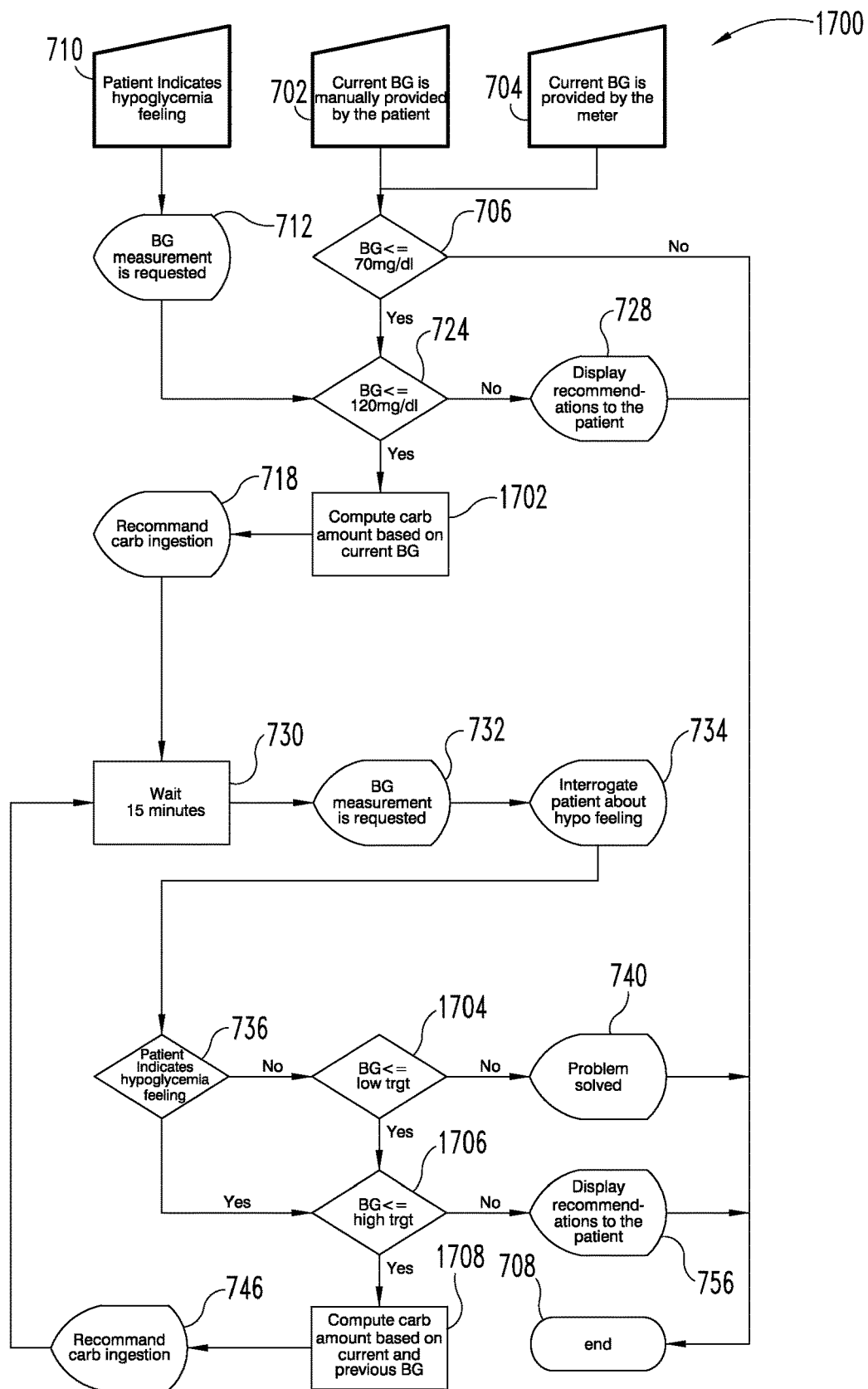
FIG. 17 is a flowchart showing a method for detecting and treating hypoglycemia, according to at least one embodiment of the present disclosure.

FIG. 17 is a flowchart 1700 that illustrates another method for detecting and treating hypoglycemia. In this method, the difference between the current blood glucose measurement and a target blood glucose level are calculated in order to determine the recommended amount of carbohydrates to ingest for the patient so as to treat the hypoglycemia. As can be seen, the flowchart 1700 in FIG. 17 shares a number of stages in common with the flowchart 700 in FIG. 7. For the sake of clarity and brevity, these stages sharing a common reference number will not be discussed in detail below, but reference is made to the previous discussion of these stages in FIG. 7. Looking at FIG. 17, instead of categorizing the amounts of carbohydrates as being small, medium, large, the meter 104 in stage 1702 simply calculates the initial or first carbohydrate amount ($n_{BU,1}$) based on the difference between the first blood glucose measurement ($BG_1$) and the desired target blood glucose level (see e.g., equation 11). In stage 1704, meter 104 compares the blood measurement to a low, relative target ($BG_{end,relative}$) so as to determine whether the surveillance phase 506 can end (see, equations 2, 9, and 10). The meter 104 in stage 1706 compares the current blood glucose level to a hypoglycemia surveillance end threshold ($BG_{hypo,end}$) to determine whether the surveillance phase can end (see, equation 1). Like in stage 1702, the meter 104 in stage 1708 simply calculates the subsequent carbohydrate amounts ($n_{BU}$) based on the difference between the current blood glucose measurement and a desired target blood glucose level.

For the sake of clarity as well as brevity, the methods were described above as being performed by the meter 104, but it should be appreciated that these methods can be performed, whole or in part, using other devices, such as the computer 102, insulin pump 106, cellular phones, etc. It should be appreciated that the meter 104 (or other devices) performs the acts in these methods through the processor 202, memory 204, I/O device 206, and/or other components. While these methods were described with respect to a patient, this term was used in the broad sense, and it should be appreciated that these methods can used by other individuals who may not be considered a patient of a particular health care provider and can be even adapted for use with human and animal subjects.

Moreover, it is contemplated that the various stages and phases described herein and illustrated in the drawings can occur in different orders than is shown. Furthermore, one or more of these acts can be combined together and other acts not described herein can be performed alongside with these methods. In other variations, instead of the patient entering in whether they feel hypoglycemic, the meter 104 or other device can actively monitor the patient so as to automatically enter the information. For example, the meter 104 can make the patient perform a test as well as check their visual and mental acuity along with other symptoms or hypoglycemia through video or speech recognition software. Questions in a questionnaire from the meter 104 about the symptoms can be simple yes/no questions or can be more specifically detailed such as via a drop down list. In another example, the meter 104 via a microphone can monitor the speech of the patient to see if the patient is experiencing a speech impediment indicative of hypoglycemia, such as slurred speech. The meter 104 can visually monitor the patient for symptoms of hypoglycemia via a video camera to see if anything visually indicates that the patient is experiencing hypoglycemia, such as excessive sweating and/or motor control problems. When the blood glucose meter 104 is used to collect data for these methods, then blood glucose value can either be processed directly if the meter hosts the hypoglycemia detection algorithm or the value is transmitted to the pump 106 or the computer 102 hosting the hypoglycemia detection algorithm. The methods described above used a 15 minute delay between glucose measurements, but it should be recognized that the delay can be more or less than 15 minutes in other embodiments.

The glucose meter 104 as described above can include discrete or continuous type glucose monitors. Moreover, the glucose meter 104 can for example measure glucose levels using electrochemical and/or photometric analysis techniques. It should be appreciated that blood glucose levels can be measured through invasive or non-invasive procedures, and various types of body fluids, like blood or interstitial fluid, can be analyzed. In one embodiment the glucose meter 104 is an ACCU-CHEK® Aviva brand glucose meter, but it should be appreciated that other types of glucose meters can be used. It should be appreciated that the blood glucose meter 104 can be configured in any number of manners. For example, the meter 104 and the insulin pump 106 can be combined together to form a single unit or various components of these systems can be spread across multiple units. The meter 104 can include additional ports to connect additional biosensors to measure a plurality of features such as body temperature, pulse, and/or blood oxygen content. It should be appreciated that commercial forms of the meter 104 can include other components and/or perform other functions than those described herein.

While the insulin pump 106 is illustrated in FIG. 1, insulin or other medication can be delivered in other manners, such as with syringes. Moreover, the above-described methods can be performed with other types of systems besides those illustrated in the drawings and/or with other combinations of devices. For example, the hypoglycemia detection and handling method can run on the insulin pump 106 directly or on the blood glucose meter 104. Note that any device allowing diabetes management such as a smart phone or a pocket PC could host a similar application.

The insulin pump 106 can be connected to the blood glucose meter 104 and/or the computer 102. The connection may be used to transmit data from the blood glucose meter 104 and/or the computer 102 to the insulin pump 106 or vice versa. For example, the electronic connection may also be used to transmit instructions from the glucose meter 104 to the insulin pump 106 regarding one or more injections of insulin from the pump into the patient. Additionally, the connection may transmit information regarding past, present, or future injections or insulin levels from the insulin pump 106 to the glucose meter 104 and/or the computer 102. Similar to the electronic connection discussed above, the connection between the glucose meter 104 and/or the insulin pump 106 may be wired or wireless and may be the same or a different type of connection than the one between the meter 104, insulin pump 106, and/or the computer 102.

While various embodiments of systems and methods for detecting and handling hypoglycemia have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A method, comprising:
    detecting hypoglycemia in a patient with a computing device;
    computing a recommended carbohydrate amount to ingest by the patient with the computing device in response to said detecting the hypoglycemia;
    outputting the recommended carbohydrate amount with the computing device; and
    performing hypoglycemia surveillance with the computing device to determine whether the recommended carbohydrate amount remedied the hypoglycemia, wherein the hypoglycemia surveillance includes:
        receiving with the computing device a second blood glucose measurement of the patient after said computing the recommended carbohydrate amount;
        determining with the computing device that the hypoglycemia has been remedied based at least on the second blood glucose measurement;
        ending said performing the hypoglycemia surveillance when the second blood glucose measurement exceeds a relative threshold that varies based on amount of carbohydrates previously consumed, wherein the relative threshold is based on a time dependent carbohydrate absorption function that increases with time.

2. The method according to claim 1, further comprising:
    calculating with the computing device the relative threshold using the following formula $$BG_{end,relative} = \gamma(t-t_1) \cdot BG_{hypo,end} + (1-\gamma(t-t_1)) \cdot BG_0$$

where:
    $BG_{end,relative}$=Relative threshold for ending the surveillance phase;
    $BG_{hypo,end}$=Threshold where hypoglycemia is considered ended;
    $\gamma(x)$=Carbohydrate absorption function for time interval x;
    t=Current time when relative threshold is being calculated;
    $t_1$=Time when first carbohydrate recommended or consumed; and
    $BG_0$=Original blood glucose measurement.

3. The method according to claim 1, further comprising:
    receiving a third blood glucose measurement;
    calculating with the computing device the relative threshold using the following formula $$BG_{end,relative} = \gamma(t-t_2) \cdot BG_{hypo,end} + (1-\gamma(t-t_2)) \cdot BG_2 + \frac{\gamma(t-t_2)}{\gamma(t_2-t_1)}(\gamma(t-t_1)-1)(BG_2-BG_1)$$

where:
    $BG_{end,relative}$=Relative threshold for ending the surveillance phase;
    $BG_{hypo,end}$=Threshold where hypoglycemia is considered ended;
    $\gamma(x)$=Carbohydrate absorption function for time interval x;
    t=Current time when relative threshold is being calculated;
    $t_n$=Time of $n^{th}$ measurement since hypoglycemia; and $BG_n = n^{th}$ blood glucose measurement since hypoglycemia.

4. The method according to claim 1, further comprising:
receiving with the computing device data indicating that the patient lacks hypoglycemia symptoms after said computing the recommended carbohydrate amount; and
determining with the computing device that the hypoglycemia has been remedied based at least on the lack of the hypoglycemia symptoms.

5. The method according to claim 1, further comprising: delaying said performing the hypoglycemia surveillance for a delay period.

6. The method according to claim 5, wherein the delay period is at least 15 minutes.

7. The method according to claim 1, wherein the recommended carbohydrate amount is selected from a group consisting of a small carbohydrate amount, a medium carbohydrate amount, and a large carbohydrate amount.

8. The method according to claim 7, wherein said computing the recommended carbohydrate amount includes selecting the small carbohydrate amount, the medium carbohydrate amount, and the large carbohydrate amount based on a very low blood glucose limit, a low blood glucose limit, and a medium-low blood glucose limit.

9. The method according to claim 8, wherein the very low blood glucose limit, the low blood glucose limit, and the medium-low blood glucose limit are respectively 60 mg/dl, 100 mg/dl, and 140 mg/dl.

10. The method according to claim 8, further comprising: calculating with the computing device the recommended carbohydrate amount using the following formula $$n_{BU} = \begin{cases} 0 & \text{if } BG_{ml} < BG \\ n_{BU,small} & \text{if } BG_1 < BG \leq BG_{ml} \\ n_{BU,medium} & \text{if } BG_{vl} < BG \leq BG_1 \\ n_{BU,large} & \text{if } BG \leq BG_{vl} \end{cases} \quad \text{Equation 21}$$

where:
$n_{BU}$=Amount of carbohydrate;
$n_{BU,small}$=Small amount of carbohydrate;
$n_{BU,medium}$=Medium amount of carbohydrate;
$n_{BU,large}$=Large amount of carbohydrate;
$BG_1$=Blood glucose measurement at hypoglycemia detection;
$B_{ml}$=Medium-low blood glucose range limit;
$BG_1$=Low blood glucose range limit; and
$BG_{vl}$=Very low blood glucose range limit.

11. The method according to claim 8, further comprising: calculating the very low blood glucose limit, the low blood glucose limit, and the medium-low blood glucose limit based on no more than the last three blood glucose measurements.

12. The method according to claim 1, further comprising: normalizing the recommended carbohydrate amount based on patient weight.

13. The method according to claim 1, further comprising: adjusting the recommended carbohydrate amount based on patient weight, or risk of fainting during hypoglycemia.

14. The method according to claim 1, further comprising: adjusting the recommended carbohydrate amount based on a total daily dose of insulin by the patient.

15. The method according to claim 1, further comprising: calculating with the computing device the recommended carbohydrate amount using the following formula $$\begin{cases} n_{BU,small} = f_n(n_{BU,TDD} + n_{BU,fainting}) \\ n_{BU,medium} = f_n(n_{BU,TDD} + n_{BU,fainting} + 1) \\ n_{BU,large} = f_n(n_{BU,TDD} + n_{BU,fainting} + 2) \end{cases}$$

where:
$n_{BU,small}$=Small amount of carbohydrate;
$n_{BU,medium}$=Medium amount of carbohydrate;
$n_{BU,large}$=Large amount of carbohydrate;
$f_n$=Normalization factor based on patient weight;
$n_{BU,fainting}$=Risk of fainting additional bread unit; and
$n_{BU,TDD}$=Additional bread unit recommended for patients with a total daily dose (TDD) of insulin $\leq$30 UI.

16. The method according to claim 1, wherein said computing the recommended carbohydrate amount includes adjusting the recommended carbohydrate amount based on prior blood glucose measurements made after detecting the hypoglycemia, prior amounts of carbohydrates ingested, and a carbohydrate absorption function.

17. The method according to claim 1, further comprising:
receiving a second blood glucose measurement after the patient ingested the second recommended amount of carbohydrate;
calculating with the computing device a second recommended carbohydrate amount using the following formula $$\begin{cases} BG_{vl,2} = \gamma(t - t_1) \cdot BG_{vl,1} + (1 - \gamma(t - t_1)) \cdot BG_1 \\ BG_{l,2} = \gamma(t - t_1) \cdot BG_{l,1} + (1 - \gamma(t - t_1)) \cdot BG_1 \\ BG_{ml,2} = \gamma(t - t_1) \cdot BG_{ml,1} + (1 - \gamma(t - t_1)) \cdot BG_1 \end{cases}$$

where:
$BG_{vl,2}$=Very low blood glucose range limit or threshold for a second amount of carbohydrate;
$BG_{l,2}$=Low blood glucose range limit or threshold for a second amount of carbohydrate;
$BG_{ml,2}$=Medium-low blood glucose range limit or threshold for a second amount of carbohydrate;
$\gamma(x)$=Carbohydrate absorption function for time interval x;
t=Current time when relative threshold is being calculated;
$t_1$=Time when first carbohydrate was consumed; and
$BG_1$=First blood glucose measurement.

18. The method according to claim 17, further comprising:
receiving a third blood glucose measurement after the patient ingested the second recommended amount of carbohydrate;
calculating with the computing device a third recommended carbohydrate amount using the following formula $$\begin{cases} BG_{vl,3} = \gamma(t-t_2) \cdot BG_{vl,3} + (1-\gamma(t-t_2)) \cdot BG_2 + \dfrac{\gamma(t-t_2)}{\gamma(t_2-t_1)}(\gamma(t-t_1)-1)(BG_2-BG_1) \\ BG_{l,3} = \gamma(t-t_2) \cdot BG_{l,3} + (1-\gamma(t-t_2)) \cdot BG_2 + \dfrac{\gamma(t-t_2)}{\gamma(t_2-t_1)}(\gamma(t-t_1)-1)(BG_2-BG_1) \\ BG_{ml,3} = \gamma(t-t_2) \cdot BG_{ml,3} + (1-\gamma(t-t_2)) \cdot BG_2 + \dfrac{\gamma(t-t_2)}{\gamma(t_2-t_1)}(\gamma(t-t_1)-1)(BG_2-BG_1) \end{cases}$$

where:
$BG_{vl,3}$=Very low blood glucose range limit or threshold for a third amount of carbohydrate (i.e., at time t3);
$BG_{l,3}$=Low blood glucose range limit or threshold for a third amount of carbohydrate (i.e., at time t3);
$BG_{ml,3}$=Medium-low blood glucose range limit or threshold for a third amount of carbohydrate (i.e., at time t3);
$\gamma(x)$=Carbohydrate absorption function for time interval x;
t=Current time when relative threshold is being calculated;
$t_n$=Time of $n^{th}$ measurement since hypoglycemia; and
$BG_n$=$n^{th}$ blood glucose measurement since hypoglycemia.

19. The method according to claim 1, further comprising: calculating subsequent amounts of carbohydrates by superimposing the effects of previous carbohydrate amounts.

20. The method according to claim 1, further comprising: calculating with the computing device the carbohydrate absorption function using the following formula $$\begin{cases} \gamma(x) = 0 & \text{if } x = 0 \\ \gamma(x) = -0.000125 \cdot x^2 + 0.022525 \cdot x + 0.0019 & \text{if } 0 < x < 78 \\ \gamma(x) = 1 & \text{if } x \geq 78 \end{cases}$$

where:
$\gamma(x)$=Carbohydrate absorption function; and
x=Time frame of interest (in minutes).

21. The method according to claim 1, further comprising: calculating with the computing device the carbohydrate absorption function using the following formula $$\begin{cases} \gamma(x) = -\dfrac{1}{t_a^2}x^2 + \dfrac{2}{t_a}x & \text{if } 0 \leq x \leq t_a \\ \gamma(x) = 1 & \text{if } x > t_a \end{cases}$$

where:
$\gamma(x)$=Carbohydrate absorption function;
x=Time frame of interest (in minutes); and
$t_a$=Total carbohydrate absorption time.

22. The method according to claim 1, further comprising: calculating with the computing device the carbohydrate absorption function using the following formula $$\begin{cases} \gamma(x) = -\dfrac{1}{t_a}x & \text{if } 0 \leq x \leq t_a \\ \gamma(x) = 1 & \text{if } x > t_a \end{cases}$$

where:
$\gamma(x)$=Carbohydrate absorption function;
x=Time frame of interest (in minutes); and
$t_a$=Total carbohydrate absorption time.

23. The method according to claim 1, further comprising: calculating with the computing device the carbohydrate absorption function using the following formula $$\gamma(x) = 1 - e^{-a \cdot x}$$

where:
$\gamma(x)$=Carbohydrate absorption function;
x=Time frame of interest (in minutes); and
a=0.03.

24. The method according to claim 1, further comprising: calculating with the computing device the carbohydrate absorption function using the following formula $$\gamma(x) = 1 - e^{-ax^2 - bx}$$

where:
$\gamma(x)$=Carbohydrate absorption function;
x=Time frame of interest (in minutes);
a=0.0004; and
b=0.015.

25. The method according to claim 1, wherein the carbohydrate absorption function is a linear function.

26. The method according to claim 1, wherein the carbohydrate absorption function is a parabolic function.

27. The method according to claim 1, wherein the carbohydrate absorption function is an exponential function.

28. The method according to claim 1, further comprising: receiving with the computing device a manual input that the patient has the symptom of hypoglycemia.

29. The method according to claim 1, further comprising: determining automatically with the computing device that the patient has the symptom of hypoglycemia.

30. The method according to claim 29, wherein said determining automatically includes analyzing results from a questionnaire to detect hypoglycemic symptoms with the computing device.

31. The method according to claim 29, wherein said determining automatically includes analyzing a video of the patient for the hypoglycemic symptoms with the computing device.

32. The method according to claim 29, wherein said determining automatically includes analyzing speech of the patient for the hypoglycemic symptoms with the computing device.

33. A computerized method of detecting and treating hypoglycemia, comprising:
receiving with a computing device a blood glucose measurement of a patient;
computing a recommended carbohydrate amount to ingest by the patient with the computing device, wherein the recommended carbohydrate amount is based at least on the blood glucose measurement of the patient, wherein said computing the recommended carbohydrate amount includes adjusting the recommended carbohydrate amount based on an amount of carbohydrates consumed by the patient during a timeframe;

outputting the recommended carbohydrate amount with the computing device to provide the patient with a visual representation of a recommendation to treat hypoglycemia and return a blood glucose level of the patient back to a non-hypoglycemic level; and performing hypoglycemia surveillance with the computing device after a delay period to determine whether the recommended carbohydrate amount remedied the hypoglycemia, wherein the recommendation and the surveillance after the delay period assists with reducing the length of or eliminating hypoglycemia and ensures resolution of hypoglycemic events, wherein the hypoglycemia surveillance includes:

receiving with the computing device a second blood glucose measurement of the patient after said computing the recommended carbohydrate amount;

determining with the computing device that the hypoglycemia has been remedied based at least on the second blood glucose measurement;

ending said performing the hypoglycemia surveillance when the second blood glucose measurement exceeds a relative threshold that varies based on amount of carbohydrates previously consumed, wherein the relative threshold is based on a time dependent carbohydrate absorption function that increases with time.

34. A computerized method of detecting and treating hypoglycemia, comprising:

detecting hypoglycemia in a patient with a computing device based at least on the patient having a symptom of hypoglycemia;

receiving with the computing device a blood glucose measurement of the patient;

computing a recommended carbohydrate amount to ingest by the patient with the computing device in response to said detecting the hypoglycemia, wherein the recommended carbohydrate amount is based at least in part on the blood glucose measurement of the patient;

outputting the recommended carbohydrate amount with the computing device to provide the patient with a visual representation of a recommendation to treat hypoglycemia and return a blood glucose level of the patient back to a non-hypoglycemic level in a manner that assists with reducing the length of or eliminating hypoglycemia and ensures resolution of hypoglycemic events; and performing hypoglycemia surveillance with the computing device to determine whether the recommended carbohydrate amount remedied the hypoglycemia, wherein the hypoglycemia surveillance includes:

receiving with the computing device a second blood glucose measurement of the patient after said computing the recommended carbohydrate amount;

determining with the computing device that the hypoglycemia has been remedied based at least on the second blood glucose measurement;

ending said performing the hypoglycemia surveillance when the second blood glucose measurement exceeds a relative threshold that varies based on amount of carbohydrates previously consumed, wherein the relative threshold is based on a time dependent carbohydrate absorption function that increases with time.

35. The method according to claim 34, wherein said computing the recommended carbohydrate amount includes adjusting the recommended carbohydrate amount based on amount of carbohydrates consumed by the patient during a timeframe.

* * * * *